(12) United States Patent
Fryer et al.

(10) Patent No.: US 11,396,539 B2
(45) Date of Patent: Jul. 26, 2022

(54) ANTI-ANGPT2 ANTIBODIES

(71) Applicant: Boehringer Ingelheim International GmbH, Ingelheim am Rhein (DE)

(72) Inventors: Ryan Michael Fryer, Brewster, NY (US); Chao Zheng, Briarcliff Manor, NY (US); Michael Dziegelewski, Newburgh, NY (US); Pankaj Gupta, Scarsdale, NY (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/911,419

(22) Filed: Jun. 25, 2020

(65) Prior Publication Data

US 2020/0407435 A1 Dec. 31, 2020

Related U.S. Application Data

(60) Provisional application No. 63/013,022, filed on Apr. 21, 2020, provisional application No. 62/867,253, filed on Jun. 27, 2019.

(51) Int. Cl.
*C07K 16/22* (2006.01)
*A61K 39/00* (2006.01)
*A61K 9/00* (2006.01)
*A61K 45/06* (2006.01)

(52) U.S. Cl.
CPC ............ *C07K 16/22* (2013.01); *A61K 9/0019* (2013.01); *A61K 45/06* (2013.01); *A61K 2039/505* (2013.01); *C07K 2317/565* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,275,149 A | 6/1981 | Litman et al. |
| 4,301,144 A | 11/1981 | Iwashita et al. |
| 4,318,980 A | 3/1982 | Boguslaski et al. |
| 4,419,446 A | 12/1983 | Howley et al. |
| 4,496,689 A | 1/1985 | Mitra |
| 4,601,978 A | 7/1986 | Karin |
| 4,640,835 A | 2/1987 | Shimizu et al. |
| 4,670,417 A | 6/1987 | Iwasaki et al. |
| 4,737,456 A | 4/1988 | Weng et al. |
| 4,791,192 A | 12/1988 | Nakagawa et al. |
| 4,816,567 A | 3/1989 | Cabilly et al. |
| 4,965,199 A | 10/1990 | Capon et al. |
| 5,888,809 A | 3/1999 | Allison |
| 6,037,454 A | 3/2000 | Jardieu et al. |
| 6,054,297 A | 4/2000 | Carter et al. |
| 6,407,213 B1 | 6/2002 | Carter et al. |
| 6,455,035 B1 * | 9/2002 | Suri .................. A61K 38/1891 424/85.1 |
| 8,834,880 B2 * | 9/2014 | Green ..................... A61P 1/16 424/141.1 |
| 9,340,609 B2 | 5/2016 | Brinkmann et al. |

FOREIGN PATENT DOCUMENTS

| | | |
|---|---|---|
| DE | 266710 A | 4/1989 |
| EP | 73657 A1 | 3/1983 |
| EP | 183070 A2 | 6/1986 |
| EP | 244234 A2 | 11/1987 |
| EP | 102226 A1 | 12/1990 |
| EP | 2832746 A1 | 2/2015 |
| WO | 9411026 A2 | 5/1994 |
| WO | 9632478 A1 | 10/1996 |
| WO | 2013134516 A1 | 9/2013 |
| WO | 2015091655 A1 | 6/2015 |
| WO | WO 2020/264065 | * 12/2020 |

OTHER PUBLICATIONS

Kyriakos, First in human Study of Nesvacumab, vol. 22, No. 6, Clinical Cancer Research, 2015.
International Search Report and Written Opinion for PCT/EP202/039477, dated Nov. 12, 2020.
Clackson, Making Antibody fragments using phage display libraris, letters to Nature, vol. 352, 199, 5 pages.
Edge, Deglycosylation of glycoproteins of Trifluromethanesulfonic Acid, Analytical Biochem., Vo. 118, 1981, p. 131-137.
Graham, Characteristics of a human cell line Transformed by DNA from Human adenovirus type 5, J. Gen Virol. vol. 36, 1977, p. 59-74.
Guss, Structure of the IgG-binding regions of streptoccal-protein G, The EMBO Journal, vol. 5, No. 7, 1986, 1567-1575.
Hakimudden, A chemical method for the deglycosylation of proteins, Archives of biochem and biophysics, vol. 259, No. 1, 1987, p. 52-57.
Higgins, Using Clustal for multiple sequence alignments, Methods in Enzymology, vol. 266, 1996, 20 pages.
Karlin, Methods for assessing the statiscal significance of molecular sequence features by using general scoring schemes, Proc. Natl. Acad., sci., vol. 87, 1990, p. 2264-2268.
Karlin, Applications and statistics for lultiple high-scoring segments in molecular sequences, Proc. Natl. Acad. Sci., vol. 90, 1993, p. 5873-5877.
Lindmark, Binding of Immunoglobulins to Protein A and Immunoglobulin Levels in Mammalian Sera, J. of Immunological Methoda, vol. 62, 1983, p. 1-13.
Maier, Abstract, Assessment of fully autmated antibody homology modeling protocols in molecular operating environment, Proteins, 2014, 12 pages.
Marks, By Passing Immunization, J. Mol. Biology, vol. 222, 1991, p. 581-597.
Mather, Culture of testicular cells in Hormone-supplemented Serum-free medium, 1982, 25 pages.

(Continued)

*Primary Examiner* — Marianne P Allen
(74) *Attorney, Agent, or Firm* — David L. Kershner

(57) ABSTRACT

The present invention relates to new anti-angiopoietin 2 (ANGPT2) neutralizing antibodies for therapeutic and diagnostic methods and composition using them.

19 Claims, 4 Drawing Sheets

Specification includes a Sequence Listing.

(56) References Cited

OTHER PUBLICATIONS

Mather, Establishment and Characterization of two distinct mouse testicular epithelial cell lines, Biology of Reproduction, vol. 23, 1980, p. 243-252.
Morimoto, Single step purification of F(ab')2 fragments of mouse monoclonal antibodies (immunoglobulins G1), J. of Biochem. and Biophysical Methods, vol. 24, 1991, p. 107-117.
Morrison, Chimeric human antibody molecules, Proc. Natl. Acad. Sci, Immunology, vol. 81, 1984, p. 6851-6855.
Myers and Miler, Cabios, Optimal Alignments in linear space, vol. 4, No. 1, 1988, p. 11-17.
Pearson and Lipman, Improved Tools for biological sequence comparison, Proc. Natl. Sci., vol. 85, 1988, p. 2444-2448.
Thotakura, Enzymatic deglycosation of glycoproteins, Methods in Enzymology, vol. 138, 1987, 10 pages.
Urlaub, Isolation of Chinese hamster cell mutants deficient in dihydrofolate reductase activity, Proc. Natl. Acad. Sci, vol. 77, No. 7, 1980, p. 4216-4220.
Carter, High level *Escherichia coli* expression and production of a bivalent humanized antibody fragment, Nautre, 1992, 5 pages.
Yaniv, Enhancing elements for activation of eukarytic promoters, Nature, vol. 297, 1982, 2 pages.
Pluckthun, Antibodies from *Escherichia coli*, Chapter 11, 1994, 47 pages.
Kohler, Continuous cultures of fused cells secreting antibody of predefined specificity, Nature, vol. 256, 1975, 3 pages.
O'sullivan, Methods for Preparation of Enzyme-Antibody Conjugates, Methods in Enzymology, vol. 73, 1981, 20 pages.
Abstract to DD266710 cited herein.
Fleer, Stable multicopy vectors for high-level secretion of recombinant human serum albumin by kluyveromyces yeasts, Nature, vol. 9, 1991, 8 pages.
Reyes, Expression of human B-interferon cDNA under the control of a thymidine kinase promoter fromherpes simplex virus, Nature, vol. 297, No. 17, 1982, 4 pages.
Stinchcomb, Isolation and characterisation of a yeast chromosomal replicator, Nature, vol. 282, No. 1, 1979, 5 pages.
Van den berg, Kluveromyces as host for heterologous geneexpression, Nature, Bio/Technology, vol. 8, 1990, 5 pages.
Zola, Using Monoclonal Antibodies: soluble antigens, Chapter 6, Monoclonal Antiboides, a Manual of Techniques, 1987, 36 pages.
An, Angiopoietin-2 in white adipose tissue improves metabolic homeostasis through enhanced angiogenesis, ELife, vol. 6, 2017, 22 pages.
Chen, Angiopoietin-2 promoter haplotypes confer an increased risk of stroke in a Chinese Han population, Clinical science, vol. 117, 2009, p. 387-395.
Chen, Functional variantion the 3-UTR of angiopoietin-1 might reduce stroke risk by interfering with the binding efficiency of microRNA211, Human Molecular Genetics, vol. 19, 2010, p. 2524-2533.
Chen, Promoter variant of angiopoietin-2 and plasma angiopoietin-2 are associated with risk of stroke,Biochem and Biophysical Research Communications, 2010, p. 212-216.
Coxon, Context dependent role of Angiopoietin-1 Inhibition in the Suppression of Angiogenesis and Tumor Growth, Molecular Cancer Therapeutics, vol. 9, 2010, p. 2641-2651.
Eleuteri, Stepwise increase of angiopoietin-2 serum levels is related to haemodynamic and functional impairment, Euro. J. of Prevention and Rehab, vol. 18, 2011, p. 607-614.
Fiedler, The tie-2 ligand Angiopoietin-2 is stored in and rapidly released upon stimupation from endothelial cell Weibel-Palade bodies, Blood, 2012, 8 pages.
Fiedler, Angiopoietin-2 sensitizes endothelial cells to TNF-x and has a crucial role in the induction of inflammation, Nature Medicine, 2006.
Gale, Angiopoietin-2 is Required for Postnatal Angiogenesis and Lymphatic Patterning, Developmental Cell, 2002, p. 411-423.
Gerstein, Identifying Novel Biomarkers for Cardiovascualr Events, Epidemiology and Prevention,2015, p. 2297-2304.

Gumik, Angiopoietin-2-induced blood-brain barrier compromise and increased stroke size are rescued by VE-PTP-dependent restoration of Tie2 signaling, Acta Neuropathol, vol. 131, 2016, p. 753-773.
Hu, Endothelial Cell-Derived Angiopoietin-2 Controls Liver regeneration as a Spatiotemporal Rheostat downloaded Jan. 24, 2018, http://scicne.science.mag.org, 5 pages.
Kim, Opposing actions of angiopoietin-2 on Tie2 signaling and FOX01 activation, The J. of clinical activation, 2016.
Lorbeer, Angiopoietin-2, its soluble receptor Tie-2 and subclinical cardiovascular disease, downloaded Dec. 1, 2014., www.bmj.com.
Papadopoulis, A Phase I First in Human study of Nesvacumab (REGN910, a Fully Human Anti-Angiopoitin-2 (Ang2) Monoclonal Antibody, Clinical Cancer Ressearch, 2015, 9 pages.
Poss, Angiopoietin-2 and outcome in patients with acute decompensated heart failure, Clin. Res. Cardiol, 2014, 8 pages.
Satchell, Angiopoietin-2 is Normally expressed in Periendothelial cells, Thromb.Haemost, vol. 86, 2001, p. 1597-8.
Satchell, Human Podocytes express Angiopoietin 1, a potential regualtor of Glomerular Vascular Endothelial Growth Factor, J. Am. Soc. Nephrol, 2002, p. 544-550.
Souma, Context-dependent functions of angiopoietin 2 are determined by the endothelial phosphatase VEPTP, PNAS, 2017, 6 pages.
Tsai, Angiopoietin-2 as Prognostic Biomarker of Major adverse cardiovascular events and all-cause mortality in chronic kidney disease, PLOS, 2015, 12 pages.
Tsai, Association of Angiopoietin-2 with renal outcome in chronic kidney disease, PLOS, vol. 9, 2014, 8 pages.
Quan, Analysis of the Association of type 2 diabetes and diabetic nephropathy, Chinese Journal of Medical Genetics, 2012, p. 72-76.
Calfee, Plasma angiopoitein-2 in clinical acute ling injury, National Institute of Health, 2012, p. 1731-1737.
Campochiaro, Enhanced Benefit in Diabetic Macular Edema from AKB-9778 Tie2 Activation Combined with Vascular Endothelial Growth Factor, American Acad., of Ophthalmology, 2016, 9 pages.
Chang, Angiopoitin-2 is associated withAlbuminuria and Microinflammation in chronic kidney disease, PLOS, vol. 9, 2013, 6 pages.
Chang, Angiopoietin-2- induced Aterial Stiffness in CKD, IASN, vol. 25, 2014, p. 1198-1209.
David, Circulating angiopoietin-2 levels increase with progress of chronic kidney disease, Nephrol. Dial Translplant, vol. 25, p. 2571-2579, 2010.
Davis, Podocyte-specific Expression of Angiopoietin-2 causes Proteinuria, JASN, 2007, 10 pages.
Dessapt, Targeted Glomular Angiopoietin-1 Therapy, JASN, vol. 25, 2014, p. 33-42.
Grenga, Select human tumor cells express Tie2, Research gate, vol. 3, 2015, vol. 3, 11 pages.
Jeansson, Angiopoietin-1 is essential in mouse vasculature during development, J. of clinical investigation, vol. 121, 2013, 12 pages.
Levy, 2001 SCCM/ESICM/ACCP/ATS/SIS Int. Sepsis Definitions, Grit Care meds, vol. 31, 2003, 7 pages.
Lukasz, Angiopoietin-2 in Adults with Congenital Heart Disease and Heart Failure, PLOS, vol. 8, 2013, 7 pages.
Statement on non proprietary name adopted by the USAN council, 2015.
Van der Heijden, Angiopoitin-2, permeability oedema, occurrence, and severity of Allards in spetic and non-septic critically ill patients, Thorax, 2008, 7 pages.
Fiedler, The Tie-2 Ligand Angiopooietin-2 is stored in and rapidly released upon stimulation from endothelial cell Weibel-Palade bodies, Hemostasis, vol. 103, 2004, 7 pages.
Lomas-Neira, Blockade of Endothelial Growth Factor, Angiopoietin-2, Reduces Indices of Ards, Shock, 2017, p. 157-165.
Monk, Anti-angiopoitin therapy with trebananib for recurrent ovarian cancer, The Lanceet, vol. 15, 2014, 10 pages.
Parikh, Excess Circulating Angiopoitin-2 may contribute to Pulmonary Vascular Leak in Sepsis in Humans, PLOS, vol. 3, 2006, 15 pages.
Peters, Abstract, Tie2 Activity via VE-PTP Inhibition for Treatment of Diabetic Kidney Disease, Abstract, 2018, 9 pages.

(56) References Cited

OTHER PUBLICATIONS

Tsai, Angiopoitin-2, Angiopoitin-1 and subclinical cardiovascular disease in chronic kidney disease, Nature, 2016, 9 pages.
Monk, Incidence and management of edema associated with trebananib, Gynecologic Oncology, vol. 13, 2013, p. 636-641.
Konishi, Utlization of Complement-Dependent Cytotoxicity to Measure Low Level of Antibodies, Clinical and Vaccine Immunology, 2008, p. 88-94.
Idusogie, Mapping of the C1q Binding Site on Rituxan, Journal of Immunology, 2000, p. 4178-4184.
Altschul, Gapped Blast and PSI-Blast: a new generation of protein database search programs, Nucleic Acids, vol. 25, 1997, p. 3389-3402.
Almagro, Abstract, Antibody Modeling Assessment, Proteins, 2011, 17 pages.
Altschul, Basic Local Alignment Search Tool, J. Mol. Biol., 1990, p. 403-410.
Brennan, Preparation of Bispecifc Antibodies by chemical Recombination of monoclonal immunoglbulin G1 fragments, downloaded from https://science.org at Boehringer Ingelheim KG Mar. 27, 2022.
Chothia and Lesk, Canonical Structures for the Hypervariable Regions of Immunoglobulins, J. Mole. Biol., 1987, vol. 196, p. 901-917.
Chothia, Domain Association in Immunoglobulin Molecules, J. Mol. Biol., vol. 186, 1985, p. 851-663.

\* cited by examiner

Figure 2

ANTI-ANGPT2 ANTIBODIES

SEQUENCE LISTING

The instant application contains a Sequence Listing which has been submitted electronically in ASCII format and is hereby incorporated by reference in its entirety. Said ASCII copy, created on Jun. 11, 2019, is named 09-0697-US-1_SL.txt and is 78,465 bytes in size.

FIELD OF THE INVENTION

This invention generally relates to anti-angiopoietin 2 (ANGPT2) neutralizing antibodies for diagnostic and therapeutic use. More specifically, anti-ANGPT2 antibodies and methods of use for the treatment of various diseases or disorders characterized by cells expressing ANGPT2 are disclosed. Pharmaceutical compositions and kits comprising the anti-ANGPT2 antibodies are also disclosed.

BACKGROUND OF THE INVENTION

Endothelial dysfunction is a hallmark of chronic kidney disease (CKD) and associated cardiovascular complications. Basic and clinical research suggest that improving renal vascular function in CKD will reduce proteinuria and slow the decline in renal function on-top-of SOC. In addition, a reduction in ANGPT2 would be expected to elicit a positive impact on cardiovascular diseases in CKD patients including in heart failure, MI, stroke, and others (Eleuteri 2011, Lukasz 2013, Poss 2015, Lorbeer 2015, Tsai 2016, Gerstein 2015, Chen 2009, Chen 2010a, Chen 2010b, Gurnik 2016).

The human ANGPT-Tie axis consists of two type-I tyrosine kinase receptors (Tie1, Tie2) and two secreted ligands (ANGPT1, ANGPT2). ANGPT1 is a Tie2 receptor agonist that induces receptor phosphorylation and activates downstream signaling pathways necessary to preserve renal vascular function, whereas ANGPT2 is a functional antagonist of ANGPT1 binding to Tie2. ANGPT1-bound Tie2 is translocated to inter-endothelial cell junctions, where multimeric ANGPT1 can form cross-endothelial complexes with Tie2 receptors from adjacent cells to stabilize the glomerular capillary structure. Intracellularly, ANGPT1-induced Tie2 phosphorylation leads to the recruitment of adaptor proteins resulting in the activation of AKT survival-promoting pathways and suppresses activation of the apoptotic pathway.

A small study investigating a role of ANGPT2 in diabetic nephropathy (DN) describe a SNP (1233 A/G) linked to a 20% elevation in circulating ANGPT2 and subsequent increase in DN severity (Quan, 2012). While no ANGPT2 blocking antibody has been tested in CKD patients, ANGPT2 mRNA expression in Pima Indians with CKD was found to be positively associated with interstitial fibrosis and intimal fibrosis. Others have shown that glomerular ANGPT2 mRNA expression is elevated in diabetic nephropathy (DN) patients as compared to levels from non-diseased kidneys (Dessapt-Baradez, 2014). However, both ANGPT1 glomerular mRNA expression (Dessapt-Baradez, 2014) and circulating protein (Chang, 2013; Chang, 2014) are unchanged in DN thereby favoring ANGPT2-bound Tie2 in the context of disease progression.

Key clinical observations linking dysregulation of the ANGPT2-Tie2 pathway with CKD were borne from studies where patients were stratified by stage (from stage 1 to ESRD/HD) and where circulating ANGPT2 was progressively elevated, correlated with arterial stiffness (Chang, 2014), and inversely correlated with a decline in inulin-measured glomular filtration rate (GFR) (David, 2010). Within a CKD 3-5 patient cohort, ANGPT2 levels were also associated with the severity of albuminuria and markers of systemic micro-inflammation (Chang, 2013). At least some of the elevated ANGPT2 present in CKD may be due to a reduction in miR-145 that normally suppresses ANGPT2 transcription, and was demonstrated to be significantly reduced in stage 3-5 CKD patients (Chen, 2013). A recent poster presented at American Society of Nephrology (Peters, 2018) showed in non-proliferative diabetic retinopathy patients with baseline albuminuria >30 mg/g that stimulation of Tie2 signaling using the vascular endothelial (VE)-protein tyrosine phosphatase, AKB-9778 (daily s.c. injection), was sufficient to reduce urine albumin-to-creatine ratio (UACR) by approximately 20% in a 3-month Phase 2A study. These results support that stimulation of the Tie2 signaling in severely albuminuric patients is sufficient to reduce CKD progression. Clinically important values for categorizing CKD patients are: eGFR of 15-60 ml/min/1.73 m$^2$ and UACR of 30 mg/g or greater.

Consistent with the concept that dysregulation of the ANGPT2-Tie2 axis contributes to CKD, pre-clinical studies demonstrate that genetic manipulation of either side of the pathway (decreased ANGPT1 or increased ANGPT2) is sufficient to elicit manifestations of the disease. In mice, conditional deletion of ANGPT1 elicits proteinuric nephropathy characterized by impaired function of the glomerular filtration barrier, albuminuria, and pathological features seen in humans with advanced diabetic nephropathy (mesangial matrix expansion and glomerulosclerosis; Jeansson, 2013). Additionally, podocyte-specific ANGPT2 overexpression results in increased albuminuria, glomerular endothelial apoptosis, and a reduction in filtration barrier proteins (Davis, 2007). Others have shown that plasma and renal expression of ANGPT2 are elevated after 5/6 nephrectomy in CD1 mice concomitant with elevated ANGPT2 staining in glomeruli (Chang, 2014). The same group demonstrated that the ANGPT2 peptibody, Li-10, after 5/6 nephrectomy blocked the vascular expression and upregulation of multiple pro-fibrotic and pro-inflammatory markers including TGFβ1, collagen subtypes, and adhesion molecules although effects on renal fibrosis were not interrogated.

ANGPT2 is predominantly expressed in tissues undergoing vascular remodeling and is elevated in the circulation in multiple diseases conditions, including CKD. Endothelial cells (EC) produce and store ANGPT2 in Weibel-Palade bodies, specialized storage granules from which ANGPT2 can be rapidly released into the circulation to bind blood and lymphatic EC Tie2 receptors (Fiedler, 2004).

Within the normal human kidney, ANGPT2 and Tie2 are expressed on ECs including those that face the glomerular basement membrane, within capillary loops, and ECs within glomeruli. Tie2 is also expressed on ECs adjacent to the podocyte foot process (Satchell, 2002).

The Tie2 agonist ligand, ANGPT1, is secreted from pericytes (Satchell, 2001) which surround and support underlying endothelial cells, and importantly also from podocytes (Satchell, 2002), specialized renal cells that comprise the glomerular filtration barrier thereby enabling cross-talk between podocytes and adjacent glomerular ECs to stabilize the glomerular capillary structure.

ANGPT2 has limited expression in normal tissues but broad expression in the actively remodeled vasculature of human tumors. Blocking ANGPT2 inhibition of Tie2 signaling is an attractive target for anti-angiogenic cancer therapy and ocular diseases with a vascular basis. Several antibodies blocking ANGPT2 binding to Tie2 have been developed for clinical use.

Specifically, based on studies with ANGPT2-selective antibodies (REGN910) administered i.v., no dose-limiting safety concerns were noted in Phase I clinical trials (Papadopoulos, 2016). A Tie2-stimulator (AKB-9778) has been tested in Phase II with no noteworthy adverse effects (AEs) (Campochiaro, 2016), and in multiple clinical studies through Phase III the dual ANGPT1/2 blocker (AMG386) has been tested with only mild and reversible AEs (Monk, 2014). However, less-selective therapeutic approaches with a lower ratio of ANGPT2:ANGPT1 blockade (e.g. AMG386, MEDI3617) were associated with an increased observation of clinical edema which may be related to dual blockade of lymphatic Tie2 receptors as both ANGPT1 and ANGPT2 function as Tie2 receptor agonists in the lymphatic vasculature. It is believed that blockade of Tie2 perturbed the normal flow of the lymphatic and venous circulation leading to extracellular fluid accumulation in general and lymph-edema specifically (Monk, 2013). A highly specific ANGPT2 blocking antibody would be expected to have a significantly diminished risk of edema; no Grade 3-4 edema was observed in Phase I studies with REGN910 (Papadopoulos, 2015).

ANGPT2 blockade may impact vascular and lymphatic responsiveness and function.

ANGPT2 reportedly plays a role in liver regeneration (Hu, 2014); reduced vascular bed plasticity; altering the healing of liver and other tissues (Gale, 2002) potentially including the tissues of the lung, adipose (An, 2017) and ovary (Coxon, 2010); and as an autocrine regulatory switch for endothelial cell inflammatory responses (Fiedler, 2006, Kim, 2016).

The role of ANGPT2 in the adult lymphatic system is not fully known. However, Tie2 is expressed on multiple leukocyte types (monocytes, neutrophils & eosinophils) and modulation of Tie2 signaling may alter immune sensitivity (Grenga, 2015).

ANGPT2 blockade is an attractive means for preventing other respiratory disorders including lung vascular hyperpermeability, pulmonary (lung) edema, acute respiratory distress syndrome (ARDS), acute lung injury (ALI), idiopathic interstitial pneumonia, Idiopathic pulmonary fibrosis (IPF) and acute exacerbation IPF, severe acute respiratory syndrome (SARS), and Middle Eastern respiratory syndrome (MERS). High plasma level of ANGPT2 plays a central role in the aberrant vascular leakage associated with plasma increase of Willebrand factor (standard marker of endothelial injury) in sepsis and ARDS (Calfee, 2012). ANGPT2 and Willebrand Factor plasma levels were significantly elevated in sepsis patients and even higher in ARDS patients (Van der Heijden, 2008). Circulating ANGPT2 was significantly elevated in humans with sepsis who also had impaired oxygenation. Serum from these patients disrupted in vitro endothelial architecture. This effect of sepsis serum was reversed by ANGPT-1 (ANGPT2 antagonist) (Parikh, 2006). In a mouse model of ARDS induced by hemorrhagic shock, the pretreatment of the mice with an anti-angpt2 antibody significantly improved lung function, blood oxygenation and survival rate (Lomas-Neira, 2016)

Increased vascular permeability (vascular hyperpermeability) contributes to many diseases, including ARDS, sepsis, severe sepsis, septic shock, cancer and inflammation. Reducing vascular hyperpermeability of the lung will reduce the accumulation of fluid in the alveolar space (lung edema) and therefore will improve the gas exchange between the lung and the vessels leading to a better oxygenation of the arterial blood. Improvement of the arterial blood oxygenation translates into a better oxygenation of all the organs (e.g., brain, heart, liver, kidney) and reduces the risk of multiple organ failure followed by death.

Increase in vascular permeability in sepsis, severe sepsis, septic shock, is also reported in several organs such as lung, kidney, liver and heart. The accumulation of fluid in these organs impairs their proper functioning (e.g. causing arrhythmia, glomerular filtration disruption, or impairment of the metabolism) and leads to organ failure followed by death.

Pulmonary (lung) edema is a condition in which the lungs fill with fluid. The most common cause of pulmonary edema is congestive heart failure. Other less common conditions that may cause pulmonary edema include sudden high blood pressure, pneumonia, kidney failure, lung damage caused by severe infection, severe sepsis of the blood, or blood poisoning caused by infection.

Acute lung injury (ALI) is a lung disorder often caused by smoke inhalation including, more recently, in the use of E-cigarette or vaping products.

Acute respiratory distress syndrome (ARDS) is a lung inflammation characterized by an increase in lung vascular permeability and/or lung edema. ARDS is often characterized as low, mild, or severe based on the degree of hypoxemia. ARDS can be triggered by several causes, e.g. can be induced by a bacterial or viral lung infection, by sepsis, inhalation of harmful substances, severe pneumonia, trauma, pancreatitis (inflammation of the pancreas), massive blood transfusions and burns. The most common cause of ARDS is sepsis.

Severe acute respiratory syndrome (SARS) is a viral respiratory illness caused by a coronavirus called SARS-associated coronavirus (SARS-CoV). SARS begins with a high fever (temperature greater than 100.4° F. [>38.0° C.]). Other symptoms may include sore throat, cough, headache, an overall feeling of discomfort, and body aches. Some people also have mild respiratory symptoms at the outset. Most patients develop pneumonia. Since 2004 until the outbreak of SARS-CoV-2 pandemic in December 2019, there have not been any known cases of SARS reported anywhere in the world.

Middle Eastern respiratory syndrome (MERS) is an illness caused by a virus (more specifically, a coronavirus) called Middle East Respiratory Syndrome Coronavirus (MERS-CoV). The disease is characterized by severe respiratory illness, including fever, cough, and shortness of breath. About three or four out of every 10 patients reported with MERS have died.

Sepsis, severe sepsis, and septic shock are disorders arising from the systemic inflammatory response to an infection (see Mitchell M. Levy et al., Crit Care Med. 2003 April; 31(4):1250-6). Sepsis is a disorder having both an infection (e.g., viral, bacterial, abdominal trauma, gut perforation) and a systemic inflammatory response. This leads to increase in vascular permeability of several organs such as kidney liver, heart and lung. Severe sepsis (sepsis with organ dysfunction) refers to sepsis with acute organ dysfunction caused by sepsis. Septic shock refers to persistent hypotension unexplained by other causes.

Thus, there is a need for high-affinity neutralizing antibody to ANGPT2 that will limit antagonistic binding of ANGPT2 to Tie2, Enhanced Tie2 signaling is expected to have many beneficial effects including, for example, stabilizing the glomerular capillary structure, reducing endothelial activation, and restoring filtration barrier integrity. In total, these beneficial effects are expected to decrease proteinuria and preserve renal function resulting in a slowed disease progression in chronic kidney disease (CKD) patients.

The beneficial effects of a high-affinity neutralizing antibody to ANGPT2 are further expected to aid in the treatment of patients afflicted with vascular hyperpermeability of the lung and associated disorders.

BRIEF SUMMARY OF THE INVENTION

The present invention provides monoclonal antibodies that specifically bind to human ANGPT2. In one aspect of the invention, the antibodies of the present invention neutralize ANGPT2. Therefore, the antibodies of the invention are useful, for example, for the treatment and/or prevention of diseases or disorders that can be alleviated by neutralizing ANGPT2.

In another aspect, the present invention provides an anti-ANGPT2 antibody, in particular a humanized anti-ANGPT2 antibody, having one or more of the properties described herein below.

In one embodiment, the present invention provides an anti-ANGPT2 antibody or an antigen-binding fragment thereof comprising:
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 17 (H-CDR3), and
a light chain variable region comprising the amino acid sequence of SEQ ID NO. 19 (L-CDR1); the amino acid sequence of SEQ ID NO. 22 (L-CDR2); and the amino acid sequence of SEQ ID NO. 24 (L-CDR3),
or
a heavy chain variable region comprising the amino acid sequence of SEQ ID NO. 14 (H-CDR1); the amino acid sequence of SEQ ID NO. 15 (H-CDR2); and the amino acid sequence of SEQ ID NO. 17 (H-CDR3); and
a light chain variable region comprising the amino acid sequence of SEQ ID NO. 19 (L-CDR1); the amino acid sequence of SEQ ID NO. 22 (L-CDR2); and the amino acid sequence of SEQ ID NO. 24 (L-CDR3),
or
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 16 (H-CDR3); and
a light chain variable region comprising the amino acid sequence of SEQ ID NO. 20 (L-CDR1); the amino acid sequence of SEQ ID NO. 23 (L-CDR2); and the amino acid sequence of SEQ ID NO. 24 (L-CDR3),
or
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 16 (H-CDR3); and
a light chain variable region comprising the amino acid sequence of SEQ ID NO. 21 (L-CDR1); the amino acid sequence of SEQ ID NO. 23 (L-CDR2); and the amino acid sequence of SEQ ID NO. 25 (L-CDR3),
or
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 16 (H-CDR3); and
a light chain variable region comprising the amino acid sequence of SEQ ID NO. 20 (L-CDR1); the amino acid sequence of SEQ ID NO. 22 (L-CDR2); and the amino acid sequence of SEQ ID NO. 24 (L-CDR3).

In another embodiment, the present invention provides an anti-ANGPT2 antibody or an antigen-binding fragment thereof comprising:
a variable heavy chain and a variable light chain comprising the amino acid sequences of SEQ ID NO. 3 and SEQ ID NO. 8, respectively,
or
a variable heavy chain and a variable light chain comprising the amino acid sequences of SEQ ID NO. 4 and SEQ ID NO. 9, respectively,
or
a variable heavy chain and a variable light chain comprising the amino acid sequences of SEQ ID NO. 5 and SEQ ID NO. 10, respectively, or
a variable heavy chain and a variable light chain comprising the amino acid sequences of SEQ ID NO. 6 and SEQ ID NO. 11, respectively, or
a variable heavy chain and a variable light chain comprising the amino acid sequences of SEQ ID NO. 7 and SEQ ID NO. 12, respectively.

In another embodiment, the present invention provides an anti-ANGPT2 antibody or an antigen-binding fragment thereof comprising:
a heavy chain comprising the amino acid sequence of SEQ ID NO. 31 and a light chain comprising the amino acid sequence of SEQ ID NO. 32,
or
a heavy chain comprising the amino acid sequence of SEQ ID NO. 33 and a light chain comprising the amino acid sequence of SEQ ID NO. 34,
or
a heavy chain comprising the amino acid sequence of SEQ ID NO. 35 and a light chain comprising the amino acid sequence of SEQ ID NO. 36,
or
a heavy chain comprising the amino acid sequence of SEQ ID NO. 37 and a light chain comprising the amino acid sequence of SEQ ID NO. 38,
or
a heavy chain comprising the amino acid sequence of SEQ ID NO. 39 and a light chain comprising the amino acid sequence of SEQ ID NO. 40.

In one embodiment, the present invention provides an anti-ANGPT2 antibody or an antigen-binding fragment thereof comprising:
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 17 (H-CDR3), or
a heavy chain variable region comprising the amino acid sequence of SEQ ID NO. 14 (H-CDR1); the amino acid sequence of SEQ ID NO. 15 (H-CDR2); and the amino acid sequence of SEQ ID NO. 17 (H-CDR3), or
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 16 (H-CDR3); or
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 16 (H-CDR3); or
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 16 (H-CDR3);

and
a heavy chain framework region comprising one to four amino acid sequences selected from the group consisting of the amino acid sequence of SEQ ID NO. 41 (H-FR1); amino acid sequence of SEQ ID NO. 42 (H-FR2); the amino acid sequence of SEQ ID NO. 43 (H-FR3); and the amino acid sequence of SEQ ID NO. 44 (H-FR4).

In another embodiment, the present invention provides an anti-ANGPT2 antibody or an antigen-binding fragment thereof comprising:
a light chain variable region comprising the amino acid sequence of SEQ ID NO. 19 (L-CDR1); the amino acid sequence of SEQ ID NO. 22 (L-CDR2); and the amino acid sequence of SEQ ID NO. 24 (L-CDR3), or
a light chain variable region comprising the amino acid sequence of SEQ ID NO. 19 (L-CDR1); the amino acid sequence of SEQ ID NO. 22 (L-CDR2); and the amino acid sequence of SEQ ID NO. 24 (L-CDR3), or
a light chain variable region comprising the amino acid sequence of SEQ ID NO. 20 (L-CDR1); the amino acid sequence of SEQ ID NO. 23 (L-CDR2); and the amino acid sequence of SEQ ID NO. 24 (L-CDR3), or
a light chain variable region comprising the amino acid sequence of SEQ ID NO. 21 (L-CDR1); the amino acid sequence of SEQ ID NO. 23 (L-CDR2); and the amino acid sequence of SEQ ID NO. 25 (L-CDR3), or
a light chain variable region comprising the amino acid sequence of SEQ ID NO. 20 (L-CDR1); the amino acid sequence of SEQ ID NO. 22 (L-CDR2); and the amino acid sequence of SEQ ID NO. 24 (L-CDR3);
and
a light chain framework region comprising one to four amino acid sequences selected from the group consisting of the amino acid sequence of SEQ ID NO. 45 (L-FR1); amino acid sequence of SEQ ID NO. 46 (L-FR2); the amino acid sequence of SEQ ID NO. 47 (L-FR3); and the amino acid sequence of SEQ ID NO. 48 (L-FR4).

In one embodiment, the present invention provides an anti-ANGPT2 antibody or antigen-binding fragment thereof that binds to at least one amino acid residue within amino acid regions 117-148 of the carboxy-terminal fibrinogen-like domain (FLD) region of human ANGPT2 with the SEQ ID NO. 50.

In another embodiment, the invention relates to an ANGTP2 antibody or antigen-binding fragment thereof that binds to SEQ ID NO: 51.

In one embodiment, the anti-ANGPT2 antibody is a humanized anti-ANGPT2 antibody.

In another embodiment, the anti-ANGPT2 antibody is a chimeric anti-ANGPT2 antibody.

In one embodiment, the present invention provides an anti-ANGPT2 antibody or an antigen-binding fragment thereof for use in medicine.

In one embodiment, the present invention provides an anti-ANGPT2 antibody or an antigen-binding fragment thereof for use in the treatment of kidney diseases.

In one embodiment, the present invention provides an anti-ANGPT2 antibody or an antigen-binding fragment thereof for use in the treatment of liver diseases.

In one embodiment, the present invention provides a pharmaceutical composition comprising an anti-ANGPT2 antibody or an antigen-binding fragment thereof and a pharmaceutically acceptable carrier.

In one embodiment, the present invention provides an anti-ANGPT2 antibody or an antigen-binding fragment thereof or a pharmaceutical composition comprising the anti-ANGPT2 antibody or an antigen-binding fragment thereof, wherein said antibody or antigen-binding fragment thereof is administered by a parenteral route, intravenous route, intravitreal route or subcutaneous route of administration.

In one embodiment, the present invention provides an isolated polynucleotide or polynucleotides comprising a sequence encoding a light chain or light chain variable region of an antibody or antigen-binding fragment thereof and a heavy chain or heavy chain variable region of an antibody or antigen-binding fragment thereof.

In one embodiment, the present invention provides an expression vector comprising an isolated polynucleotide or polynucleotides encoding a light chain or light chain variable region of an antibody or antigen-binding fragment thereof and a heavy chain or heavy chain variable region of an antibody or antigen-binding fragment thereof.

In one embodiment, the present invention provides a viral vector comprising an isolated polynucleotide or polynucleotides encoding a light chain or light chain variable region of an antibody or antigen-binding fragment thereof and a heavy chain or heavy chain variable region of an antibody or antigen-binding fragment thereof.

In one embodiment, the present invention provides a host cell comprising an expression vector or an isolated polynucleotide or polynucleotides encoding a light chain or light chain variable region of an antibody or antigen-binding fragment thereof and a heavy chain or heavy chain variable region of an antibody or antigen-binding fragment thereof.

In one embodiment, the present invention provides a method for producing an anti-ANGPT2 antibody or an antigen-binding fragment thereof comprising: obtaining a host cell comprising an expression vector or an isolated polynucleotide or polynucleotides encoding a light chain or light chain variable region of an antibody or antigen-binding fragment thereof and a heavy chain or heavy chain variable region of an antibody or antigen-binding fragment thereof; and cultivating the host cell.

In one embodiment, the method for producing an anti-ANGPT2 antibody or antigen-binding fragment thereof further comprises recovering and purifying the anti-ANGPT2 antibody or antigen-binding fragment thereof.

In another embodiment, the present invention relates to an isolated polynucleotide or polynucleotides comprising:
a sequence encoding a heavy chain as shown in SEQ ID NO: 31 or a heavy chain variable region as shown in SEQ ID NO: 3; and a sequence encoding a light chain as shown in SEQ ID NO. 32 or alight chain variable region as shown in SEQ ID NO: 8, or
an isolated polynucleotide or polynucleotides comprising a sequence encoding a heavy chain as shown in SEQ ID NO: 33 or a heavy chain variable region as shown in SEQ ID NO: 4; and a sequence encoding a light chain as shown in SEQ ID NO. 34 or a light chain variable region as shown in SEQ ID NO: 9,
or
an isolated polynucleotide or polynucleotides comprising a sequence encoding a heavy chain as shown in SEQ ID NO: 35 or a heavy chain variable region as shown in SEQ ID NO: 5; and a sequence encoding a light chain as shown in SEQ ID NO. 36 or a light chain variable region as shown in SEQ ID NO: 10,
or
an isolated polynucleotide or polynucleotides comprising a sequence encoding a heavy chain as shown in SEQ ID NO: 37 or a heavy chain variable region as shown in SEQ ID NO:

6; and a sequence encoding a light chain as shown in SEQ ID NO. 38 or a light chain variable region as shown in SEQ ID NO: 11, or an isolated polynucleotide or polynucleotides comprising a sequence encoding a heavy chain as shown in SEQ ID NO: 39 or a heavy chain variable region as shown in SEQ ID NO: 7; and a sequence encoding a light chain as shown in SEQ ID NO. 40 or a light chain variable region as shown in SEQ ID NO: 12.

Non-limiting examples of diseases, disorders, or conditions that can be alleviated by the anti-ANGPT2 antibodies of the invention include cardiac hypertrophy, myocardial infarction, ischemia, ischemic reperfusion injury, stroke hypertension, pulmonary arterial hypertension, idiopathic pulmonary arterial hypertension, trauma induced brain disorders, asthma, chronic obstructive pulmonary disease (COPD), rheumatoid arthritis, inflammatory bowel disease, multiple sclerosis, -preeclampsia and pregnancy-induced hypertension, sepsis, severe sepsis, septic shock, non-alcoholic steatohepatitis (NASH), cirrhosis, minimal change disease, focal segmental glomerulosclerosis (FSGS), nephrotic syndrome, diabetic kidney disease (DKD), chronic kidney disease (CKD), diabetic renal insufficiency, end stage renal disease, ischemia or an ischemic reperfusion injury, cancer, hepatocellular carcinoma, idiopathic pulmonary fibrosis (IPF), emphysema, acute lung injury (ALI), acute respiratory disease syndrome (ARDS), severe acute respiratory syndrome (SARS), Middle Eastern respiratory syndrome (MERS), vascular hyperpermeability (and associated disorders), acute kidney injury (AKI), renal cell carcinoma, heart failure, lupus nephritis, Raynaud's, pancreatitis, peripheral artery disease, congenital heart disease, Dengue virus, malaria, hantavirus, edema, regeneration, lupus, interstitial lung disease, scleroderma, retinopathies, diabetic nephropathy, portal hypertension, varices growth, and liver transplantation.

DETAILED DESCRIPTION OF THE INVENTION

Figure 1A:
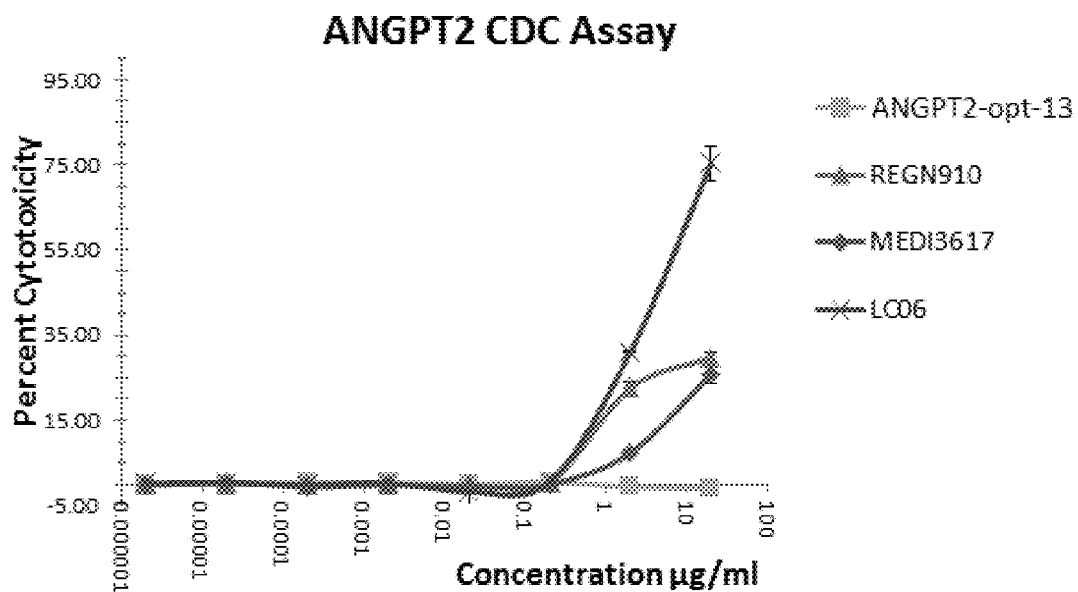
FIGS. 1A and 1B show the results (duplicate studies) of an angiopoietin 2 cell-based complement-dependent cytotoxicity (CDC) assay showing the cytotoxicity of ANGPT2-opt-13 (-□-), an analog of REGN910 (nesvacumab) (-Δ-), an analog of MEDI3617 (-◇-), and LC06 (-*-).

The generalized structure of antibodies or immunoglobulin is well known to those of skill in the art, these molecules are heterotetrameric glycoproteins, typically of about 150,000 Daltons, composed of two identical light (L) chains and two identical heavy (H) chains. Each light chain is covalently linked to a heavy chain by one disulfide bond to form a heterodimer, and the heterotrimeric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$=variable heavy chain), followed by three or four constant domains ($C_{H1}$, $C_{H2}$, $C_{H3}$, and $C_{H4}$), as well as a hinge region between $C_{H1}$ and $C_{H2}$. Each light chain has two domains, an amino-terminal variable domain ($V_L$=variable light chain) and a carboxy-terminal constant domain ($C_L$). The $V_L$ domain associates non-covalently with the $V_H$ domain, whereas the $C_L$ domain is commonly covalently linked to the $C_{H1}$ domain via a disulfide bond. Particular amino acid residues are believed to form an interface between the light and heavy chain variable domains (Chothia et al., 1985, J. Mol. Biol. 186:651-663.)

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5$^{th}$ Ed. Public Health Service, National Institutes of Health, Bethesda, Md., whereas HVLs are structurally defined according to the three-dimensional structure of the variable domain, as described by Chothia and Lesk, 1987, J. Mol. Biol. 196: 901-917. Where these two methods result in slightly different identifications of a CDR, the structural definition is preferred. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains are not directly involved in antigen binding, but contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody-dependent cellular cytotoxicity (ADCC), complement-dependent cytotoxicity (CDC) and antibody-dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$, respectively. The heavy chain constant domains that correspond to the different classes of immunoglobulins are called α, δ, ε, γ, and μ, respectively. The subunit structures and three-dimensional configurations of the classes of native immunoglobulins are well known.

The terms, "antibody", "anti-angiopoietin 2 antibody", "anti-ANGPT2 antibody", "humanized anti-ANGPT2 antibody", and "variant humanized anti-ANGPT2 antibody" are used herein in the broadest sense and specifically encompass monoclonal antibodies (including full length monoclonal antibodies), multispecific antibodies (e.g., bispecific antibodies), antibodies with minor modifications such as N- or C-terminal truncations and antibody fragments such as variable domains and other portions of antibodies that exhibit a desired biological activity, e.g., ANGPT2 binding.

The term "monoclonal antibody" (mAb) refers to an antibody of a population of substantially homogeneous antibodies; that is, the individual antibodies in that population are identical except for naturally occurring mutations that may be present in minor amounts. Monoclonal antibodies are highly specific, being directed against a single antigenic determinant, an "epitope". Therefore, the modifier "monoclonal" is indicative of a substantially homogeneous population of antibodies directed to the identical epitope and is not to be construed as requiring production of the antibody by any particular method. It should be understood that monoclonal antibodies can be made by any technique or methodology known in the art; including e.g., the hybridoma method (Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germline sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The terms, "antibody fragment", "antigen binding fragment", "anti-ANGPT2 antibody fragment", "humanized anti-ANGPT2 antibody fragment", "variant humanized anti-ANGPT2 antibody fragment" refer to a portion of a full length anti-ANGPT2 antibody, in which a variable region or a functional capability is retained, for example, specific ANGPT2 epitope binding. Examples of antibody fragments include, but are not limited to, a Fab, Fab', $F(ab')_2$, Fd, Fv, scFv and scFv-Fc fragment, a diabody, alinear antibody, a single-chain antibody, a minibody, a diabody formed from antibody fragments, and multispecific antibodies formed from antibody fragments.

Full length antibodies can be treated with enzymes such as papain or pepsin to generate useful antibody fragments. Papain digestion is used to produce two identical antigen-binding antibody fragments called "Fab" fragments, each with a single antigen-binding site, and a residual "Fc" fragment. The Fab fragment also contains the constant domain of the light chain and the $C_{H1}$ domain of the heavy chain. Pepsin treatment yields a $F(ab')_2$ fragment that has two antigen-binding sites and is still capable of cross-linking antigen.

Fab' fragments differ from Fab fragments by the presence of additional residues including one or more cysteines from the antibody hinge region at the C-terminus of the $C_{H1}$ domain. $F(ab')_2$ antibody fragments are pairs of Fab' fragments linked by cysteine residues in the hinge region. Other chemical couplings of antibody fragments are also known.

"Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

A "single-chain Fv" or "scFv" antibody fragment is a single chain Fv variant comprising the $V_H$ and $V_L$ domains of an antibody where the domains are present in a single polypeptide chain. The single chain Fv is capable of recognizing and binding antigen. The scFv polypeptide may optionally also contain a polypeptide linker positioned between the $V_H$ and $V_L$ domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

Other recognized antibody fragments include those that comprise a pair of tandem Fd segments ($V_H$-$C_{H1}$-$V_H$-$C_{H1}$) to form a pair of antigen binding regions. These "linear antibodies" can be bispecific or monospecific as described in, for example, Zapata et al. 1995, Protein Eng. 8(10):1057-1062.

A humanized antibody or a humanized antibody fragment is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or HVLs of a non-human antibody, inserted between the FRs of a human heavy or light chain variable domain.

The present invention describes specific humanized anti-ANGPT2 antibodies which contain CDRs derived from the chimeric lead CL-209881 inserted between the FRs of human germline sequence heavy and light chain variable domains.

In one aspect, a humanized anti-ANGPT2 antibody comprises substantially all of at least one, and typically two, variable domains (such as contained, for example, in Fab, Fab', F(ab')2, Fabc, and Fv fragments) in which all, or substantially all, of the CDRs correspond to those of a non-human immunoglobulin, and specifically herein, the CDRs are murine sequences of the chimeric lead CL-209881, and the FRs are those of a human immunoglobulin consensus or germline sequence. In another aspect, a humanized anti-ANGPT2 antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_{H1}$, hinge, $C_{H2}$, $C_{H3}$, and/or $C_{H4}$ regions of the heavy chain, as appropriate.

A humanized anti-ANGPT2 antibody can be selected from any class of immunoglobulins, including IgM, IgG, IgD, IgA and IgE, and any isotype, including $IgG_1$, $IgG_2$, $IgG_3$, $IgG_4$, $IgA_1$ and $IgA_2$. For example, the constant domain can be a complement fixing constant domain where it is desired that the humanized antibody exhibit cytotoxic activity, and the isotype is typically $IgG_1$. Where such cytotoxic activity is not desirable, the constant domain may be of another isotype, e.g., $IgG_2$. An alternative humanized anti-ANGPT2 antibody can comprise sequences from more than one immunoglobulin class or isotype, and selecting particular constant domains to optimize desired effector functions is within the ordinary skill in the art.

The FRs and CDRs, or HVLs, of a humanized anti-ANGPT2 antibody need not correspond precisely to the parental sequences. For example, one or more residues in the import CDR, or HVL, or the consensus or germline FR sequence may be altered (e.g., mutagenized) by substitution, insertion or deletion such that the resulting amino acid residue is no longer identical to the original residue in the corresponding position in either parental sequence but the antibody nevertheless retains the function of binding to ANGPT2. Such alteration typically will not be extensive and will be conservative alterations. Usually, at least 75% of the humanized antibody residues will correspond to those of the parental consensus or germline FR and import CDR sequences, more often at least 90%, and most frequently greater than 95%, or greater than 98% or greater than 99%.

Immunoglobulin residues that affect the interface between heavy and light chain variable regions ("the $V_L$-$V_H$ interface") are those that affect the proximity or orientation of the two chains with respect to one another. Certain residues that may be involved in interchain interactions include $V_L$ residues 34, 36, 38, 44, 46, 87, 89, 91, 96, and 98 and $V_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). U.S. Pat. No. 6,407,213 also discusses that residues such as $V_L$ residues 43 and 85, and $V_H$ residues 43 and 60 also may be involved in this interaction. While these residues are indicated for human IgG only, they are applicable across species. Important antibody residues that are reasonably expected to be involved in interchain interactions are selected for substitution into the consensus sequence.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of humanized anti-ANGPT2 antibodies. See, for example, U.S. Pat. Nos. 6,037,454 and 6,054,297.

Human germline sequences are found naturally in human population. A combination of those germline genes generates antibody diversity. Germline antibody sequences for the light chain of the antibody come from conserved human germline kappa or lambda v-genes and j-genes. Similarly, the heavy chain sequences come from germline v-, d- and j-genes (LeFranc, M-P, and LeFranc, G, "The Immunoglobulin Facts Book" Academic Press, 2001).

An "isolated" antibody is one that has been identified and separated and/or recovered from a component of its natural environment. Contaminant components of the antibody's natural environment are those materials that may interfere with diagnostic or therapeutic uses of the antibody, and can be enzymes, hormones, or other proteinaceous or nonproteinaceous solutes. In one aspect, the antibody will be purified to at least greater than 95% isolation by weight of antibody.

An isolated antibody includes an antibody in situ within recombinant cells in which it is produced, since at least one component of the antibody's natural environment will not be present. Ordinarily however, an isolated antibody will be prepared by at least one purification step in which the recombinant cellular material is removed.

The term "antibody performance" refers to factors/properties that contribute to antibody recognition of antigen or the effectiveness of an antibody in vivo. Changes in the amino acid sequence of an antibody can affect antibody properties such as folding, and can influence physical factors such as initial rate of antibody binding to antigen ($k_a$), dissociation constant of the antibody from antigen ($k_d$), affinity constant of the antibody for the antigen (Kd), conformation of the antibody, protein stability, and half-life of the antibody.

The term "neutralizing antibody" or "blocking antibody" refers to an antibody whose binding to ANGPT2 blocks the interaction between ANGPT2 and its receptor (Tie-2) and/or results in inhibition of at least one biological function of ANGPT2. It will be understood that the inhibition caused by an ANGPT2 neutralizing or blocking antibody need not be complete so long as it is detectable using an appropriate assay. Exemplary assays for detecting ANGPT2 inhibition are described herein or a known in the art.

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers.

The term "mammal" for purposes of treatment refers to any animal classified as a mammal, including humans, domesticated and farm animals, and zoo, sports, or pet animals, such as dogs, horses, cats, cows, and the like. Preferably, the mammal is human.

A "disorder", as used herein, is any condition that would benefit from treatment with a humanized anti-ANGPT2 antibody described herein. This includes chronic and acute disorders or diseases including those pathological conditions that predispose the mammal to the disorder in question.

As used herein, the term "ANGPT2-associated disorder" or "ANGPT2-associated disease" refers to a condition in which modification or activation of cells expressing ANGPT2 is indicated. An ANGPT2-associated disorder includes diseases and disorders such as age-related macular degeneration, geographic atrophy, diabetic retinopathy, diabetic macular edema, retinitis pigmentosa, inherited retinal dystrophy, inherited macular dystrophy, myopic degeneration, retinal vein occlusions, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, and traumatic retinopathy as well as prodromal and mild-to-moderate Alzheimer's diseases, delaying disease progression of patients with Alzheimer's disease, Huntington's disease, Parkinson's disease, major depressive disorder, schizophrenia, cognitive impairment associated with schizophrenia, prevention of first-episode psychosis in individuals with attenuated psychosis syndrome, prevention of relapse in patients with schizophrenia, treatment-resistant depression, and metabolic diseases like hyperphagia, obesity or metabolic syndrome.

An ANGPT2-associated disorder also includes cardiac hypertrophy, myocardial infarction, ischemia, ischemic reperfusion injury, stroke hypertension, pulmonary arterial hypertension, idiopathic pulmonary arterial hypertension, trauma induced brain disorders, asthma, chronic obstructive pulmonary disease (COPD), rheumatoid arthritis, inflammatory bowel disease, multiple sclerosis, -preeclampsia and pregnancy-induced hypertension, sepsis, severe sepsis, septic shock, non-alcoholic steatohepatitis (NASH), cirrhosis, minimal change disease, focal segmental glomerulosclerosis (FSGS), nephrotic syndrome, diabetic kidney disease (DKD), chronic kidney disease (CKD), diabetic renal insufficiency, end stage renal disease, ischemia or an ischemic reperfusion injury, cancer, hepatocellular carcinoma, idiopathic pulmonary fibrosis (IPF), emphysema, acute lung injury (ALI), acute respiratory disease syndrome (ARDS), severe acute respiratory syndrome (SARS), Middle Eastern respiratory syndrome (MERS), vascular hyperpermeability (and associated disorders), acute kidney injury, renal cell carcinoma, heart failure, lupus nephritis, Raynaud's, pancreatitis, peripheral artery disease, congenital heart disease, Dengue virus, malaria, hantavirus, edema, regeneration, lupus, interstitial lung disease, scleroderma, retinopathies, diabetic nephropathy, portal hypertension, varices growth, and liver transplantation.

The term "intravitreal injection" has its normal meaning in the art and refers to introduction of an anti-ANGPT2 antibody or antigen-binding fragment thereof into the vitreous of a patient.

The term "specifically binds," or the like, means that an anti-ANGPT2 antibody or antigen-binding fragment thereof forms a complex with an antigen that is relatively stable under physiologic conditions. Methods for determining whether two molecules specifically bind are described herein or a known in the art and include, for example, equilibrium dialysis, surface plasmon resonance, and the like. In one embodiment, specific binding is characterized by a $K_D$ of about $1 \times 10^{-8}$ M or less according to the Affinity Binding method described in the Examples section herein. In another embodiment, specific binding is characterized by a $K_D$ of about $1 \times 10^{-9}$ M or less according to the Affinity Binding method described in the Examples section herein. An isolated antibody that specifically binds human Ang-2 may, however, have cross-reactivity to other antigens, such as ANGPT2-2 molecules from other species. Moreover, an isolated antibody may be substantially free of other cellular material and/or chemicals.

The term "subcutaneous administration" refers to introduction of an anti-ANGPT2 antibody or antigen-binding fragment thereof under the skin of an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue.

The term "therapeutically effective amount" is used to refer to an amount of an anti-ANGPT2 antibody or antigen-binding fragment thereof that relieves or ameliorates one or more of the symptoms of the disorder being treated. In doing so, it is that amount that has a beneficial patient outcome. In one aspect, the therapeutically effective amount has a neuroprotective or neuroregenerative effect. In another aspect, the therapeutically effective amount refers to a target serum concentration that has been shown to be effective in, for example, slowing disease progression. Efficacy can be measured in conventional ways, depending on the condition to be treated. For example, efficacy can be measured by determining the response rates, e.g. restoration of vision or by assessing the time of delay until disease progression.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an anti-ANGPT2 antibody or antigen-binding fragment thereof prior to or following the onset of a symptom of a disease or disorder thereby preventing or removing one or more signs of the disease or disorder. As another example, the term includes the administration of an anti-ANGPT2 antibody or antigen-binding fragment thereof after clinical manifestation of the disease to combat the symptoms of the disease. Further, administration of an anti-ANGPT2 antibody or antigen-binding fragment thereof after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the anti-ANGPT2 antibody composition or antigen-binding fragment thereof, the result should be considered an effective treatment of the underlying disorder regardless of whether all the symptoms of the disorder are alleviated or not.

The term "package insert" is used to refer to instructions customarily included in commercial packages of therapeutic products, that contain information about the indications, usage, administration, contraindications and/or warnings concerning the use of such therapeutic products.

Antibodies

Described and disclosed herein are anti-ANGPT2 antibodies, in particular humanized anti-ANGPT2 antibodies as well as compositions and articles of manufacture comprising anti-ANGPT2 antibodies of the present invention. Also described are antigen-binding fragments of an anti-ANGPT2 antibody. The anti-ANGPT2 antibodies and anti-gen-binding fragments thereof can be used in the treatment of a variety of diseases or disorders characterized by reduced activity of the ANGPT2 pathway. An anti-ANGPT2 antibody and an antigen-binding fragment thereof each include at least a portion that specifically recognizes an ANGPT2 epitope.

In an initial characterization, the anti-ANGPT2 chimeric lead CL-209881 was selected based on its superior antibody performance. A library of variants was generated by placing the CDRs of the chimeric lead into FRs of the human consensus heavy and light chain variable domains and furthermore by engineering the FRs with different alterations.

This resulted in 33 sequences which underwent further optimization and liability-fixing to provide 6 final candidates with the enhanced properties as disclosed herein. The sequences of the antibody of the invention as shown below:

```
VH SEQUENCES
CL-209881_VH (chimeric lead), variable heavy chain,
                                                    SEQ ID NO: 1
QVQLKQSGAELVKPGSSVKISCRASGYIFIDYFINWVKQRPGQGLEWIGKIGPGSGSSSNEKF

KGKATLTADKSSSTAYMQLSSLTSEDSAVYFCAREAFDYDGDYYGMAYWGQGTSVTVSS

ANGPT2-opt-1 (humanized) variable heavy chain,
                                                    SEQ ID NO: 3
QVQLVQSGAEVKKPGSSVKVSCKASGYIFIDYFINWVRQAPGQGLEWMGKIGPGSGSSSNE

KFKGRVTITADKSTSTAYMELSSLRSEDTAVYYCAREAFDYEGDYYGMAYWGQGTLVTVSS

ANGPT2-opt-2 (humanized) variable heavy chain,
                                                    SEQ ID NO: 4
QVQLVQSGAEVKKPGSSVKVSCKASGYIFIEYFINWVRQAPGQGLEWMGKIGPGSGSSSNE

KFKGRVTITADKSTSTAYMELSSLRSEDTAVYYCAREAFDYEGDYYGMAYWGQGTLVTVSS

ANGPT2-opt-13 (humanized) variable heavy chain,
                                                    SEQ ID NO: 5
QVQLVQSGAEVKKPGSSVKVSCKASGYIFIDYFINWVRQAPGQGLEWMGKIGPGSGSSSNE

KFKGRVTITADKSTSTAYMELSSLRSEDTAVYYCAREAFDYDGDYYGMAYWGQGTLVTVSS

ANGPT2-opt-19 (humanized) variable heavy chain,
                                                    SEQ ID NO: 6
QVQLVQSGAEVKKPGSSVKVSCKASGYIFIDYFINWVRQAPGQGLEWMGKIGPGSGSSSNE

KFKGRVTITADKSTSTAYMELSSLRSEDTAVYYCAREAFDYDGDYYGMAYWGQGTLVTVSS

ANGPT2-opt-31 (humanized) variable heavy chain,
                                                    SEQ ID NO: 7
QVQLVQSGAEVKKPGSSVKVSCKASGYIFIDYFINWVRQAPGQGLEWMGKIGPGSGSSSNE

KFKGRVTITADKSTSTAYMELSSLRSEDTAVYYCAREAFDYDGDYYGMAYWGQGTLVTVSS

VL SEQUENCES
CL-209881_VL (chimeric lead), variable light chain,
                                                    SEQ ID NO: 2
DIVMTQSPSSLSVSAGEKVTMSCKSSQSLLNSGNQKNFLAWYQQKPGQPPKLLIYGASTRESG

VPDRFTGSGSGTDFTLTITSVQAEDLAVYYCQNDHSYPITFGSGTKLEIK

ANGPT2-opt-1 (humanized) variable light chain,
                                                    SEQ ID NO: 8
EIVMTQSPATLSVSPGERATLSCKSSQSLLASGNQKNFLAWYQQKPGQAPRLLIYGASTRESGI

PARFSGSGSGTEFTLTISSLQSEDFAVYYCQNDHSYPITFGQGTKLEIK

ANGPT2-opt-2 (humanized) variable light chain,
                                                    SEQ ID NO: 9
EIVMTQSPATLSVSPGERATLSCKSSQSLLASGNQKNFLAWYQQKPGQAPRLLIYGASTRESGI

PARFSGSGSGTEFTLTISSLQSEDFAVYYCQNDHSYPITFGQGTKLEIK

ANGPT2-opt-13 (humanized) variable light chain,
                                                    SEQ ID NO: 10
EIVMTQSPATLSVSPGERATLSCKSSQSLLSSGNQKSFLAWYQQKPGQAPRLLIYGASTRETGI

PARFSGSGSGTEFTLTISSLQSEDFAVYYCQNDHSYPITFGQGTKLEIK

ANGPT2-opt-19 (humanized) variable light chain,
                                                    SEQ ID NO: 11
EIVMTQSPATLSVSPGERATLSCRASQSVLSSGNQKSFLAWYQQKPGQAPRLLIYGASTRETGI

PARFSGSGSGTEFTLTISSLQSEDFAVYYCQQDHSYPITFGQGTKLEIK

ANGPT2-opt-31 (humanized) variable light chain,
                                                    SEQ ID NO: 12
EIVMTQSPATLSVSPGERATLSCKSSQSLLSSGNQKSFLAWYQQKPGQAPRLLIYGASTRESGI

PARFSGSGSGTEFTLTISSLQSEDFAVYYCQNDHSYPITFGQGTKLEIK
```

The underlined portions of the sequences described above correspond to the CDR regions of the variable light and heavy chain regions.

Humanized anti-ANGPT2 antibodies of the present invention are those that have the light and heavy chain sequences as set forth in the following table.

TABLE 1

FULL LENGTH LC AND HC SEQUENCES OF THE HUMANIZED ANTI-ANGPT2 ANTIBODIES.

| Antibody | Sequence | SEQ ID NO: |
|---|---|---|
| ANGPT2-opt-1 (humanized) heavy chain | QVQLVQSGAEVKKPGSSVKVSCKAS<u>GYIFIDYFIN</u>WVR QAPGQGLEWMG<u>KIGPGSGSSSSNEKFKG</u>RVTITADKS TSTAYMELSSLRSEDTAVYYCAR<u>EAFDYEGDYYGMAY</u> WGQGTLVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEPK SCDKTHTCPPCPAPELLGGPSVFLFPPKPKDTLMISRT PEVTCVVVDVSHEDPEVKFNWYVDGVEVHNAKTKPRE EQYNSTYRVVSVLTVLHQDWLNGKEYKCKVSNKALPA PIEKTISKAKGQPREPQVYTLPPSREEMTKNQVSLTCL VKGFYPSDIAVEWESNGQPENNYKTTPPVLDSDGSFF LYSKLTVDKSRWQQGNVFSCSVMHEALHNHYTQKSLS LSPG | 31 |
| ANGPT2-opt-2 (humanized) heavy chain | QVQLVQSGAEVKKPGSSVKVSCKAS<u>GYIFIEYFIN</u>WVR QAPGQGLEWMG<u>KIGPGSGSSSSNEKFKG</u>RVTITADKS TSTAYMELSSLRSEDTAVYYCAR<u>EAFDYEGDYYGMAY</u> WGQGTLVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEPK SCDKTHTCPPCPAPELLGGPSVFLFPPKPKDTLMISRT PEVTCVVVDVSHEDPEVKFNWYVDGVEVHNAKTKPRE EQYNSTYRVVSVLTVLHQDWLNGKEYKCKVSNKALPA PIEKTISKAKGQPREPQVYTLPPSREEMTKNQVSLTCL VKGFYPSDIAVEWESNGQPENNYKTTPPVLDSDGSFF LYSKLTVDKSRWQQGNVFSCSVMHEALHNHYTQKSLS LSPG | 33 |
| ANGPT-opt-13 (humanized) heavy chain | QVQLVQSGAEVKKPGSSVKVSCKAS<u>GYIFIDYFIN</u>WVR QAPGQGLEWMG<u>KIGPGSGSSSSNEKFKG</u>RVTITADKS TSTAYMELSSLRSEDTAVYYCAR<u>EAFDYDGDYYGMAY</u> WGQGTLVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEPK SCDKTHTCPPCPAPELLGGPSVFLFPPKPKDTLMISRT PEVTCVVVDVSHEDPEVKFNWYVDGVEVHNAKTKPRE EQYNSTYRVVSVLTVLHQDWLNGKEYKCKVSNKALPA PIEKTISKAKGQPREPQVYTLPPSREEMTKNQVSLTCL VKGFYPSDIAVEWESNGQPENNYKTTPPVLDSDGSFF LYSKLTVDKSRWQQGNVFSCSVMHEALHNHYTQKSLS LSPG | 35 |
| ANGPT2-opt-19 (humanized) heavy chain | QVQLVQSGAEVKKPGSSVKVSCKAS<u>GYIFIDYFIN</u>WVR QAPGQGLEWMG<u>KIGPGSGSSSSNEKFKG</u>RVTITADKS TSTAYMELSSLRSEDTAVYYCAR<u>EAFDYDGDYYGMAY</u> WGQGTLVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEPK SCDKTHTCPPCPAPELLGGPSVFLFPPKPKDTLMISRT PEVTCVVVDVSHEDPEVKFNWYVDGVEVHNAKTKPRE EQYNSTYRVVSVLTVLHQDWLNGKEYKCKVSNKALPA PIEKTISKAKGQPREPQVYTLPPSREEMTKNQVSLTCL VKGFYPSDIAVEWESNGQPENNYKTTPPVLDSDGSFF LYSKLTVDKSRWQQGNVFSCSVMHEALHNHYTQKSLS LSPG | 37 |
| ANGPT2-opt-31 (humanized) heavy chain | QVQLVQSGAEVKKPGSSVKVSCKAS<u>GYIFIDYFIN</u>WVR QAPGQGLEWMG<u>KIGPGSGSSSSNEKFKG</u>RVTITADKS TSTAYMELSSLRSEDTAVYYCAR<u>EAFDYDGDYYGMAY</u> WGQGTLVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEPK SCDKTHTCPPCPAPELLGGPSVFLFPPKPKDTLMISRT PEVTCVVVDVSHEDPEVKFNWYVDGVEVHNAKTKPRE EQYNSTYRVVSVLTVLHQDWLNGKEYKCKVSNKALPA PIEKTISKAKGQPREPQVYTLPPSREEMTKNQVSLTCL VKGFYPSDIAVEWESNGQPENNYKTTPPVLDSDGSFF LYSKLTVDKSRWQQGNVFSCSVMHEALHNHYTQKSLS LSPG | 39 |

TABLE 1 -continued

FULL LENGTH LC AND HC SEQUENCES OF THE HUMANIZED ANTI-ANGPT2 ANTIBODIES.

| Antibody | Sequence | SEQ ID NO: |
|---|---|---|
| ANGPT2-opt-1 (humanized) light chain | EIVMTQSPATLSVSPGERATLSCKSSQSLLASGNQKNF LAWYQQKPGQAPRLLIYGASTRESGIPARFSGSGSGT EFTLTISSLQSEDFAVYYCQNDHSYPITFGQGTKLEIKR TVAAPSVFIFPPSDEQLKSGTASVVCLLNNFYPREAKV QWKVDNALQSGNSQESVTEQDSKDSTYSLSSTLTLSK ADYEKHKVYACEVTHQGLSSPVTKSFNRGEC | 32 |
| ANGPT2-opt-2 (humanized) light chain | EIVMTQSPATLSVSPGERATLSCKSSQSLLASGNQKNF LAWYQQKPGQAPRLLIYGASTRESGIPARFSGSGSGT EFTLTISSLQSEDFAVYYCQNDHSYPITFGQGTKLEIKR TVAAPSVFIFPPSDEQLKSGTASVVCLLNNFYPREAKV QWKVDNALQSGNSQESVTEQDSKDSTYSLSSTLTLSK ADYEKHKVYACEVTHQGLSSPVTKSFNRGEC | 34 |
| ANGPT2-opt-13 (humanized) light chain | EIVMTQSPATLSVSPGERATLSCKSSQSLLSSGNQKSF LAWYQQKPGQAPRLLIYGASTRETGIPARFSGSGSGT EFTLTISSLQSEDFAVYYCQNDHSYPITFGQGTKLEIKR TVAAPSVFIFPPSDEQLKSGTASVVCLLNNFYPREAKV QWKVDNALQSGNSQESVTEQDSKDSTYSLSSTLTLSK ADYEKHKVYACEVTHQGLSSPVTKSFNRGEC | 36 |
| ANGPT2-opt-19 (humanized) light chain | EIVMTQSPATLSVSPGERATLSCRASQSVLSSGNQKSF LAWYQQKPGQAPRLLIYGASTRETGIPARFSGSGSGT EFTLTISSLQSEDFAVYYCQQDHSYPITFGQGTKLEIKR TVAAPSVFIFPPSDEQLKSGTASVVCLLNNFYPREAKV QWKVDNALQSGNSQESVTEQDSKDSTYSLSSTLTLSK ADYEKHKVYACEVTHQGLSSPVTKSFNRGEC | 38 |
| ANGPT2-opt-31 (humanized) light chain | EIVMTQSPATLSVSPGERATLSCKSSQSLLSSGNQKSF LAWYQQKPGQAPRLLIYGASTRESGIPARFSGSGSGT EFTLTISSLQSEDFAVYYCQNDHSYPITFGQGTKLEIKR TVAAPSVFIFPPSDEQLKSGTASVVCLLNNFYPREAKV QWKVDNALQSGNSQESVTEQDSKDSTYSLSSTLTLSK ADYEKHKVYACEVTHQGLSSPVTKSFNRGEC | 40 |

TABLE 2

CDRs OF THE HUMANIZED ANTI-ANGPT2 ANTIBODIES ACCORDING TO THE CHEMICAL COMPUTING GROUP (CCG), KLABATHA AND CHOTHIA NUMBERING SYSTEMS.

| Antibody | Sequence | SEQ ID NO: |
|---|---|---|
| H-CDR1 from CL-209881 ANGPT2-opt-1 ANGPT2-opt-13 ANGPT2-opt-19 ANGPT2-opt-31 | GYIFIDYFIN | 13 |
| H-CDR1 from ANGP12-opt-2 | GYIFIEYFIN | 14 |
| H-CDR2 from CL-209881 ANGPT2-opt-1 ANGP12-opt-2 ANGPT2-opt-13 ANGPT2-opt-19 ANGPT2-opt-31 | KIGPGSGSSSSNEKFKG | 15 |
| H-CDR3 from CL-209881 ANGPT2-opt-13 ANGPT2-opt-19 ANGPT2-opt-31 | EAFDYDGDYYGMAY | 16 |
| H-CDR3 from ANGPT2-opt-1 ANGP12-opt-2 | EAFDYEGDYYGMAY | 17 |
| L-CDR1 from CL-209881 | KSSQSLLNSGNQKNFLA | 18 |
| L-CDR1 from ANGPT2-opt-1 ANGP12-opt-2 | KSSQSLLASGNQKNFLA | 19 |
| L-CDR1 from ANGPT2-opt-13 ANGPT2-opt-31 | KSSQSLLSSGNQKSFLA | 20 |
| L-CDR1 from ANGPT2-opt-19 | RASQSVLSSGNQKSFLA | 21 |
| L-CDR2 from CL-209881 ANGPT2-opt-1 ANGP12-opt-2 ANGPT2-opt-31 | GASTRES | 22 |
| L-CDR2 from ANGPT2-opt-13 ANGPT2-opt-19 | GASTRET | 23 |
| L-CDR3 from CL-209881 ANGPT2-opt-1 ANGP12-opt-2 | QNDHSYPIT | 24 |

TABLE 2 -continued

CDRs OF THE HUMANIZED ANTI-ANGPT2 ANTIBODIES
ACCORDING TO THE CHEMICAL COMPUTING GROUP (CCG),
KLABATHA AND CHOTHIA NUMBERING SYSTEMS.

| Antibody | Sequence | SEQ ID NO: |
|---|---|---|
| ANGPT2-opt-13 | | |
| ANGPT2-opt-31 | | |
| L-CDR3 from BI00767086 | QQDHSYPIT | 25 |
| H-CDR1 for SEQ ID NO. 15 (Kabat) | DYFIN | 26 |
| H-CDR1 for SEQ ID NO. 16 (Kabat) | EYFIN | 27 |
| H-CDR1 for SEQ ID NO. 15 (Chothia) | *GYIFIDY* | 28 |
| H-CDR1 for SEQ ID NO. 16 (Chothia) | *GYIFIEY* | 29 |
| H-CDR2 for SEQ ID NO. 17 (Chothia) | *GPGSGS* | 30 |

Above CDRs as per the Chemical Computing Group (COG) numbering are underlined (Almagro et al., Proteins 2011; 79:3050-3066 and Maier et al, Proteins 2014; 82:1599-1610). The Kabat numbering for the sequences is denoted by the bold text and the Chothia numbering system by the italicized text.

Humanization and Amino Acid Sequence Variants

Further variant ANGPT2 antibodies and antibody fragments can be engineered based on the set of CDRs depicted in SEQ ID NOs: 13 to 25. It is to be understood that in the variant ANGPT2 antibodies and antibody fragments the amino acid sequence of the CDRs remain unchanged but the surrounding regions, e.g., FR regions can be engineered. Amino acid sequence variants of the anti-ANGPT2 antibody can be prepared by introducing appropriate nucleotide changes into the anti-ANGPT2 antibody DNA, or by peptide synthesis. Such variants include, for example, deletions from, and/or insertions into and/or substitutions of, residues within the amino acid sequences of the anti-ANGPT2 antibodies of the examples herein. Any combination of deletions, insertions, and substitutions is made to arrive at the final construct, provided that the final construct possesses the desired characteristics. The amino acid changes also may alter post-translational processes of the humanized or variant anti-ANGPT2 antibody, such as changing the number or position of glycosylation sites.

In some embodiments, the present invention includes ANGPT2-antibodies or antibody fragments thereof having a variable heavy chain and a variable light chain, wherein the variable heavy chain amino acid sequence and the variable light chain amino acid sequence are at least 80%, at least 90%, at least 95%, at least 98%, or at least 99% identical to the amino acid sequences of SEQ ID NOs: 3 or 8; or 4 or 9; or 5 or 10; or 6 or 11; or 7 or 12, respectively.

In some embodiments, the present invention includes anti-ANGPT2 antibodies or antibody fragments thereof having a heavy chain and alight chain, wherein the heavy chain amino acid sequence and the light chain amino acid sequence are at least 80%, at least 90%, at least 95%, at least 98%, or at least 99% identical to the amino acid sequences of SEQ ID NOs: 31 or 32; or 33 or 34; or 35 or 36; or 37 or 38; or 39 or 40, respectively.

Another type of amino acid variant of the antibody involves altering the original glycosylation pattern of the antibody. The term "altering" in this context means deleting one or more carbohydrate moieties found in the antibody, and/or adding one or more glycosylation sites that were not previously present in the antibody.

In some aspects, the present invention includes nucleic acid molecules that encode the amino acid sequence variants of the anti-ANGPT2 antibodies described herein. Nucleic acid molecules encoding amino acid sequence variants of the anti-ANGPT2 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-ANGPT2 antibody.

In certain embodiments, the anti-ANGPT2 antibody is an antibody fragment. There are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from E. coli and chemically coupled to form F(ab')$_2$ fragments (see, e.g., Carter et al., 1992, Bio/Technology 10:163-167). By another approach, F(ab')$_2$ fragments can be isolated directly from recombinant host cell culture. Other techniques for the production of antibody fragments will be apparent to the skilled practitioner.

The anti-ANGPT2 antibodies and antigen-binding fragments thereof can include modifications.

In certain embodiments, it may be desirable to use an anti-ANGPT2 antibody fragment, rather than an intact antibody. It may be desirable to modify the antibody fragment in order to increase its serum half-life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis. See, e.g., WO 96/32478.

In other embodiments, the present invention includes covalent modifications of the anti-ANGPT2 antibodies. Covalent modifications include modification of cysteinyl residues, histidyl residues, lysinyl and amino-terminal residues, arginyl residues, tyrosyl residues, carboxyl side groups (aspartyl or glutamyl), glutaminyl and asparaginyl residues, or seryl, or threonyl residues. Another type of covalent modification involves chemically or enzymatically coupling glycosides to the antibody. Such modifications may be made by chemical synthesis or by enzymatic or chemical cleavage of the antibody, if applicable. Other types of covalent modifications of the antibody can be introduced into the molecule by reacting targeted amino acid residues of the antibody with an organic derivatizing agent that is capable of reacting with selected side chains or the amino- or carboxy-terminal residues.

Removal of any carbohydrate moieties present on the antibody can be accomplished chemically or enzymatically. Chemical deglycosylation is described by Hakimuddin et al., 1987, Arch. Biochem. Biophys. 259:52 and by Edge et al., 1981, Anal. Biochem., 118:131. Enzymatic cleavage of carbohydrate moieties on antibodies can be achieved by the use of a variety of endo- and exo-glycosidases as described by Thotakura et al., 1987, Meth. Enzymol 138:350.

Another type of useful covalent modification comprises linking the antibody to one of a variety of nonproteinaceous polymers, e.g., polyethylene glycol, polypropylene glycol, or polyoxyalkylenes, in the manner set forth in one or more of U.S. Pat. Nos. 4,640,835, 4,496,689, 4,301,144, 4,670, 417, 4,791,192 and 4,179,337.

Epitope Binding

In another aspect, the invention relates to an antibody that recognizes a specific "ANGPT2 antigen epitope" and "ANGPT2 epitope". In particular, the antibody of the invention binds to an epitope in the terminal fibrinogen-like domain (FLD) domain of human ANGTP2 with the SEQ ID NO: 50.

In one aspect, the invention relates to a ANGTP2 antibody or antigen-binding fragment thereof that binds to at least one amino acid residue within the amino acid region 117-148 of the FLD domain of human ANGTP2 (which is in the C-terminus of the full length protein of human ANGPT2) as set forth in SEQ ID NO: 50.

In another aspect, the invention relates to an ANGTP2 antibody or antigen-binding fragment thereof that binds to SEQ ID NO: 51.

The sequences SEQ ID NOs: 50 and 51 are depicted in the following table.

TABLE 3

FLD domain of human ANGPT2 and ANGPT2 epitope of the antibodies of the invention.

| Name | Sequence | | | SEQ ID NO: |
|------|----------|---|---|------------|
| FLD domain of human ANGTP2 | KEEQISFRDC STEEIKAYCD FQRTWKEYKV NQQRYVLKIH EELNYRIHLK TKDGDNDKCI LNGMYYPQRQ KATTMMIRPA | AEVFKSGHTT MEAGGGGWTI GFGNPSGEYW LKDWEGNEAY GLTGTAGKIS CKCSQMLTGG NTNKFNGIKW DF | NGIYTLTFPN IQRREDGSVD LGNEFVSQLT SLYEHFYLSS SISQPGNDFS WWFDACGPSN YYWKGSGYSL | SEQ ID NO: 50 |
| ANGTP2 epitope | YLSSEELNYR ND | IHLKGLTGTA | GKISSISQPG | SEQ ID NO: 51 |

As used herein, the terms "ANGPT2 antigen epitope" and "ANGPT2 epitope" refer to a molecule (e.g., a peptide) or a fragment of a molecule capable of binding to an anti-ANGPT2 antibody or antigen-binding fragment thereof. These terms further include, for example, an ANGPT2 antigenic determinant recognized by any of the antibodies or antibody fragments of the present invention, which has a light and heavy chain CDR combination selected from light chain CDRs of the SEQ ID Nos. 18 to 25 and heavy chain CDRs of the SEQ ID Nos. 13 to 17. In a further embodiment, the ANGPT2 antigenic determinant recognized by any of the antibodies or antibody fragments of the present invention, has a light and heavy chain CDR combination selected from light chain CDRs of the SEQ ID Nos. 19 to 25 and heavy chain CDRs of the SEQ ID Nos. 13 to 17.

ANGPT2 antigen epitopes can be included in proteins, protein fragments, peptides or the like. The epitopes are most commonly proteins, short oligopeptides, oligopeptide mimics (i.e., organic compounds that mimic antibody binding properties of the ANGPT2 antigen), or combinations thereof.

It has been found that the antibodies or antibody fragments of the present invention bind to a unique epitope in the FLD domain of human ANGPT2. Preferably, an anti-ANGPT2 antibody or antigen-binding fragment thereof binds to at least one amino acid residue within the amino acid region of the FLD domain of human ANGPT2 with the SEQ ID NO: 50.

In one embodiment, the present invention provides an anti-ANGPT2 antibody or antigen-binding fragment thereof that binds to at least one amino acid residue within amino acid regions of the FLD domain of human ANGPT2 with the SEQ ID NO: 51.

Thus, in the context of epitope binding, the phrase "binds within amino acid region X-Y . . . " means that the anti-ANGPT2 antibody or antigen-binding fragment thereof binds to at least one amino acid residue within the amino acid region specified in the sequence.

If for example, the anti-ANGPT2 antibody or antigen-binding fragment thereof binds to at least one amino acid residue within amino acid region 117 to 148, this has the meaning that the anti-ANGPT2 antibody or antigen-binding fragment thereof binds to at least one amino acid residue either within amino acid region 117 to 148 of the FLD domain of human ANPT2 with the SEQ ID NO: 50.

In another aspect, an anti-ANGPT2 antibody or antigen-binding fragment thereof binds to at least 10%, 20%, 30%, 40%, 50%, 60%, 70%, 80%, 85%, 90%, 95%, or 100% of the amino acid residues within amino acid regions 117-148 of the FLD domain of human ANGPT2 with the SEQ ID NO: 50.

Figure 2:
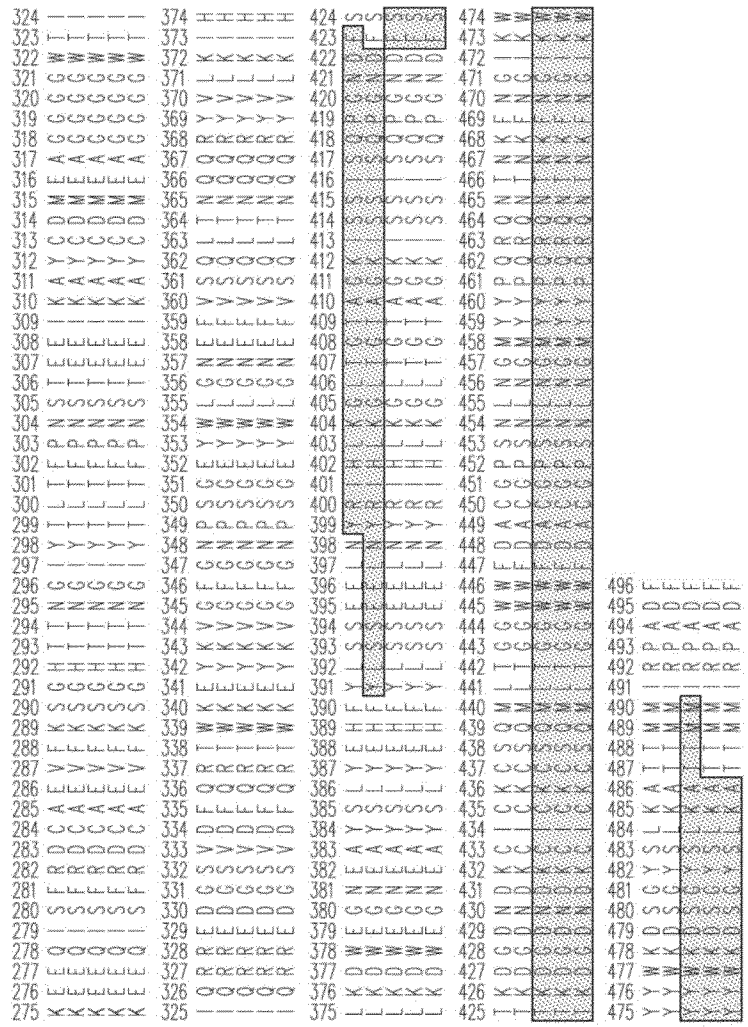
FIG. 2 shows the epitope mapping to the FLD domain of anti-ANGPT2 bodies (SEQ ID NO: 59): chimeric lead CL-209881, ANGPT2-opt-13, an analog of nesvacumab, an analog of MEDI3617, and LC06. Specific binding sites for each molecule to the extracellular FLD domain of human ANGTP2 (SEQ ID NO: 59) are highlighted in dark grey.

FIG. 2 shows the results of epitope mapping for chimeric lead CL_209881, ANGPT2-opt-13 (an exemplary anti-ANGTP2 of the invention), a nesvacumab analog (where the lysine residue at position 219 is replaced with arginine, K219R), a MED3617 analog, and LC06. Specific binding sites for each molecule to the extracellular FLD domain of human ANGTP2 are highlighted in dark grey. Chimeric lead CL_209881 and ANGPT2-opt-13 (which was derived from the CL_209881) bind to an epitope that is distinct from the epitopes which bind the comparator antibodies.

The anti-ANGPT2 antibodies of the invention block the physical interaction between ANGPT2 and Tie2 expressing cells, and show complete inhibition of Tie2 phosphorylation mediated by full length ANGPT2 oligomer.

The anti-ANGPT2 antibodies of the invention are highly selective. There is no binding to human ANGPT1 FLD domain detected at the highest tested concentration (500 nM). Furthermore, the anti-ANGPT2 antibodies of the invention did not show non-specific binding to charged or hydrophobic surfaces when tested up to 1 µM.

Affinity binding data show that the anti-ANGTP2 antibodies of the invention have a high-affinity and are highly selective for blocking ANGPT2. For example, the anti-ANGPT2 antibodies of the invention have high binding affinity to human, cyno and rabbit ANGPT2 FLD domains.

Since the anti-ANGPT2 antibodies of the invention do not show binding affinity to recombinant mouse ANGPT2 proteins, mouse efficacy studies were performed with a mouse cross-reactive tool molecule (the nesvacumab analog) that recognizes the mouse ANGPT2 FLD domain ($K_D$: ~200 µM). In those studies using a disease- and mechanistically-relevant pre-clinical model (db/db UNX mice), treatment with the nesvacumab analog for 8-10 weeks, and at dose levels suppressing free circulating ANGPT2, resulted in a significant elevation of glomerular Tie2 phosphorylation and a reduction in the disease phenotype including significant improvements in renal structure (decreases in glomerulosclerosis and interstitial fibrosis).

While the anti-ANGPT2 antibodies of the invention could not be tested in mouse for reductions in nephropathy progression, the weak binding affinity of the anti-ANGPT2 antibodies of the invention to the rat ANGPT2 FLD domain enabled testing the molecule in an acute mechanistic in vivo permeability model in rat known as a Miles assay. The Miles assay takes advantage of VEGF-mediated ANGPT2 release from storage granules in endothelial cells that results in a rapid vascular destabilization in vivo, and an effect that can be quantified; the model was validated with the nesvacumab analog. In the rat Miles assay, the anti-permeability effect of ANGPT2-opt-13 was observed (49% reduction in permeability vs. IgG control), confirming the in vivo activity of the molecule to block ANGPT2-mediated vascular destabilization.

The cytoxicities of the anti-ANGPT2 antibodies of the invention are investigated using an ANGPT2 cell-based complement-dependent cytotoxicity (CDC) assay. The CDC assay included two ANGPT1/ANGPT2 cross-reactive antibodies (MEDI3617 analog and LC06), a comparator antibody that does not cross-react with ANGPT1 (nesvacumab analog), and an exemplary anti-ANGPT2 antibody of the invention (ANGPT2-opt-13).

The results of the CDC assay (FIGS. 1A and 1B), show that the ANGPT1/ANGPT2 cross-reactive comparator antibodies (MED3617 analog and LC06) and ANGPT2 specific comparator antibody (nesvacumab analog) all exhibit higher cytotoxicities than does ANGPT2-opt-13.

Therapeutic Uses

In one embodiment, the anti-ANGPT2 antibodies of the invention, or antigen-binding fragments thereof are useful for treating or preventing diseases or disorders that can be alleviated by neutralizing ANGPT2 ("the ANGPT2 related diseases or disorders").

In another embodiment, the anti-ANGPT2 antibodies of the invention, or antigen-binding fragments thereof, are useful as a medicament.

In one embodiment, the ANGPT2 disease or disorder is selected from the group consisting of An ANGPT2-associated disorder also includes cardiac hypertrophy, myocardial infarction, ischemia, ischemic reperfusion injury, stroke hypertension, pulmonary arterial hypertension, idiopathic pulmonary arterial hypertension, trauma induced brain disorders, asthma, chronic obstructive pulmonary disease (COPD), rheumatoid arthritis, inflammatory bowel disease, multiple sclerosis, -preeclampsia and pregnancy-induced hypertension, sepsis, severe sepsis, septic shock, non-alcoholic steatohepatitis (NASH), cirrhosis, minimal change disease, focal segmental glomerulosclerosis (FSGS), nephrotic syndrome, diabetic kidney disease (DKD), chronic kidney disease (CKD), diabetic renal insufficiency, end stage renal disease, ischemia or an ischemic reperfusion injury, cancer, hepatocellular carcinoma, idiopathic pulmonary fibrosis (IPF), emphysema, acute lung injury (ALI), acute respiratory disease syndrome (ARDS), severe acute respiratory syndrome (SARS), Middle Eastern respiratory syndrome (MERS), vascular hyperpermeability (and associated disorders), acute kidney injury, renal cell carcinoma, heart failure, lupus nephritis, Raynaud's, pancreatitis, peripheral artery disease, congenital heart disease, Dengue virus, malaria, hantavirus, edema, regeneration, lupus, interstitial lung disease, scleroderma, retinopathies, diabetic nephropathy, portal hypertension, varices growth, and liver transplantation.

In one embodiment, the present invention relates to a method for treating NASH, cirrhosis, portal hypertension, varices growth variceal hemorrhage, and hepatic encephalopathy.

In another embodiment, the present invention relates to a method for treating chronic kidney disease. The term "chronic kidney disease" generally refers to a patient having reducing kidney function as measured by glomular filtration rate (GFR). An estimated GFR (eGFR) of 90 or greater (Stage 1) is considered normal kidney function; an eGFR or 89 to 60 (Stage 2) is considered mild loss of kidney function; an eGFR of 59 to 45 (Stage 3a) is considered mild to moderate loss of kidney function; an eGFR of 44 to 30 (Stage 3b) is considered moderate to severe loss of kidney function; and a GFR of 29 to 15 (Stage 4) is considered severe loss of kidney function.

In another embodiment, the CKD patients have an albumin-to-creatine ratio (UACR) $\geq 30$ mg/g and an eGFR of 20-75 ml/min/1.73 m$^2$ or 15-60 ml/min/1.73 m$^2$.

In one embodiment, the invention relates to the treatment of Stage 2 chronic kidney disease; in another embodiment, the invention relates to the treatment of Stage 3a chronic kidney disease; in another embodiment, the invention relates to the treatment of Stage 3b chronic kidney disease; and in another embodiment, the invention relates to the treatment of Stage 4 chronic kidney disease.

In another embodiment, the invention relates to the treatment of chronic kidney disease in a patient having an $\geq$eGFR 60; in another embodiment, the invention relates to the treatment of chronic kidney disease in a patient having an $\geq$eGFR 45; in another embodiment, the invention relates to the treatment of chronic kidney disease in a patient having an $\geq$eGFR 30; and in another embodiment, the invention relates to the treatment of chronic kidney disease in a patient having an $\geq$eGFR 20.

In another embodiment, the invention relates to the treatment of chronic kidney disease in a patient having an eGFR of 20-75 ml/min/1.73 m2.

In another embodiment, the invention relates to a method for treating chronic kidney disease in a patient having a UACR $\geq$30 mg/g.

In another embodiment, the invention relates to a method for treating chronic kidney disease in rapid progressing (fast progressor) patients. As used herein, the term rapid progressing CKD patients have an eGFR of 20-75 ml/min/1.73 m2 and a decline $\geq$3 ml/min/1.73 m2/year. In another embodiment, the rapid progressing CKD patients have an eGFR of 20-75 ml/min/1.73 m2 and a decline $\geq$4 ml/min/1.73 m2/year.

In another embodiment, the invention relates to a method for reducing progression to end stage renal disease (ESRD), dialysis and/or cardiovascular events in a CKD patent having an eGFR 20-75 ml/min/1.73 m2.

In another embodiment, the invention relates to a method for reducing risk of a cardiovascular event in a CKD patient, for example, a patient having an eGFR 20-75 ml/min/1.73 m2.

In another embodiment, the present invention relates to a method for treating diabetic nephropathy.

In another embodiment, the present invention relates to methods for treating vascular hyperpermeability and/or its associated disorders. These include (i) respiratory disorders associated with vascular hyperpermeability that are not primarily caused by an infection (Group 1), and (ii) respiratory disorders associated with vascular hyperpermeability caused by certain bacterial, viral, or fungal parasites infections (Group 2).

Nonlimiting respiratory disorders associated with vascular hyperpermeability of Group 1 include pulmonary (lung) edema, idiopathic interstitial pneumonia, IPF and acute exacerbation IPF, ARDS not infection-related, and ALI; and Nonlimiting respiratory disorders associated with vascular hyperpermeability of Group 2 include ARDS related to an infection, SARS, MERS, sepsis, severe sepsis, and septic shock.

ARDS, not infection-related, is understood as ARDS which is not triggered or caused by an infection, such as ARDS caused by inhalation of harmful substances (e.g. toxic smoke), trauma, pancreatitis, gastric juice reflux, massive blood transfusions or burns.

ARDS, infection-related, is understood as ARDS which is triggered or caused by an infection, such as ARDS caused by sepsis or severe pneumonia.

In one embodiment, the present invention relates to treatment of vascular hyperpermeability.

In another embodiment, the present invention relates treatment of vascular hyperpermeability arising from or caused by a bacterial infection including, but not limited to, *Legionella pneumophila, Haemophilus influenzae, Sterptococcus pneumonia, Klebsiella, Mycoplasma* pneumonia, and *Staphylococcus aureus*.

In another embodiment, the present invention relates treatment of vascular hyperpermeability arising from or caused by a fungal infection including, but not limited to, fungal pneumonia and parasitic pneumonia.

In another embodiment, the present invention relates treatment of vascular hyperpermeability arising from or caused by a viral infection including, not limited to, influenza H1N1, respiratory syncytial virus, parainfluenza, adenovirus, and human coronavirus (CoV) infections such as SARS-CoV, SARS-CoV-2 and MERS-CoV.

In another embodiment, the present invention relates to treatment of vascular hyperpermeability associated with ALI, ARDS, or SARS.

Non-Therapeutic Uses

The antibodies described herein are useful as affinity purification agents. In this process, the antibodies are immobilized on a solid phase such a Protein A resin, using methods well known in the art. The immobilized antibody is contacted with a sample containing the ANGPT2 protein (or fragment thereof) to be purified, and thereafter the support is washed with a suitable solvent that will remove substantially all the material in the sample except the ANGPT2 protein, which is bound to the immobilized antibody. Finally, the support is washed with another suitable solvent that will release the ANGPT2 protein from the antibody.

Anti-ANGPT2 antibodies are also useful in diagnostic assays to detect and/or quantify ANGPT2 protein, for example, detecting ANGPT2 expression in specific cells, tissues, or serum.

It will be advantageous in some embodiments, for example, for diagnostic purposes to label the antibody with a detectable moiety. Numerous detectable labels are available, including radioisotopes, fluorescent labels, enzyme substrate labels and the like. The label may be indirectly conjugated with the antibody using various known techniques. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (such as digoxin) and one of the different types of labels mentioned above is conjugated with an anti-hapten antibody (e.g., anti-digoxin antibody). Thus, indirect conjugation of the label with the antibody can be achieved.

Exemplary radioisotopes labels include $^{35}S$, $^{14}C$, $^{125}I$, $^{3}H$, and $^{131}I$. The antibody can be labeled with the radioisotope, using the techniques described in, for example, Current Protocols in Immunology, Volumes 1 and 2, 1991, Coligen et al., Ed. Wiley-Interscience, New York, N.Y., Pubs. Radioactivity can be measured, for example, by scintillation counting.

Exemplary fluorescent labels include labels derived from rare earth chelates (europium chelates) or fluorescein and its derivatives, rhodamine and its derivatives, dansyl, Lissamine, phycoerythrin, and Texas Red are available. The fluorescent labels can be conjugated to the antibody via known techniques, such as those disclosed in Current Protocols in Immunology, supra, for example. Fluorescence can be quantified using a fluorimeter.

There are various well-characterized enzyme-substrate labels known in the art (see, e.g., U.S. Pat. No. 4,275,149 for a review). The enzyme generally catalyzes a chemical alteration of the chromogenic substrate that can be measured using various techniques. For example, alteration may be a color change in a substrate that can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured, using a chemiluminometer, for example, or donates energy to a fluorescent acceptor.

Examples of enzymatic labels include luciferases such as firefly luciferase and bacterial luciferase (U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (such as glucose oxidase, galactose oxidase, and glucose-6-phosphate dehydrogenase), heterocydic oxidases (such as uricase and xanthine oxidase), lactoperoxidase, microperoxidase, and the like. Techniques for conjugating enzymes to antibodies are described, for example, in O'Sullivan et al., 1981, Methods for the Preparation of Enzyme-Antibody Conjugates for use in Enzyme Immunoassay, in Methods in Enzym. (J. Langone & H. Van Vunakis, eds.), Academic press, N.Y., 73: 147-166.

Examples of enzyme-substrate combinations include, for example: Horseradish peroxidase (HRPO) with hydrogen peroxidase as a substrate, wherein the hydrogen peroxidase oxidizes a dye precursor such as orthophenylene diamine (OPD) or 3,3',5,5'-tetramethyl benzidine hydrochloride (TMB); alkaline phosphatase (AP) with para-Nitrophenyl phosphate as chromogenic substrate; and β-D-galactosidase (β-D-Gal) with a chromogenic substrate such as p-nitrophenyl-β-D-galactosidase or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

In another embodiment, the anti-ANGPT2 antibody is used unlabeled and detected with a labeled antibody that binds the anti-ANGPT2 antibody.

The antibodies described herein may be employed in any known assay method, such as competitive binding assays, direct and indirect sandwich assays, and immunoprecipitation assays. See, e.g., Zola, Monoclonal Antibodies: A Manual of Techniques, pp. 147-158 (CRC Press, Inc. 1987).

Diagnostic Kits.

A humanized anti-ANGPT2 antibody can be used in a diagnostic kit, i.e., a packaged combination of reagents in predetermined amounts with instructions for performing the diagnostic assay. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Diagnostic Kits

An anti-ANGPT2 antibody can be used in a diagnostic kit, i.e., a packaged combination of reagents in predetermined amounts with instructions for performing the diagnostic assay. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Compositions and Administration Thereof

A composition comprising an anti-ANGPT2 antibody or an antigen-binding fragment thereof can be administered to a subject having or at risk of the ANGPT2 related diseases or disorders described herein. The invention further provides for the use of an anti-ANGPT2 antibody or an antigen-binding fragment thereof in the manufacture of a medicament for prevention or treatment of an ANGPT2 disease. The term "subject" as used herein means any mammalian patient to which an anti-ANGPT2 antibody or an antigen-binding fragment thereof can be administered, including, e.g., humans and certain non-human mammals, such as primates, and dogs. Subjects specifically intended for treatment using the methods described herein include humans. The anti-ANGPT2 antibody or an antigen-binding fragment thereof can be administered either alone or in combination with other compositions.

Preferred antibodies for use in such pharmaceutical compositions are those that comprise the antibody according to the invention.

Various delivery systems are known and can be used to administer the anti-ANGPT2 antibody or an antigen-binding fragment thereof. Methods of introduction include but are not limited to intravitreal, eye drops, intradermal, intramuscular, intraperitoneal, intravenous, subcutaneous, intranasal, epidural, and oral routes. The anti-ANGPT2 antibody or an antigen-binding fragment thereof can be administered, for example by infusion, bolus or injection, and can be administered together with other biologically active agents. Administration can be systemic or local. In preferred embodiments, the administration is by intravitreal injection. Formulations for such injections may be prepared in, for example, prefilled syringes.

An anti-ANGPT2 antibody or an antigen-binding fragment thereof can be administered as pharmaceutical compositions comprising a therapeutically effective amount of the anti-ANGPT2 antibody or an antigen-binding fragment thereof and one or more pharmaceutically compatible ingredients.

In typical embodiments, the pharmaceutical composition is formulated in accordance with routine procedures as a pharmaceutical composition adapted for intravenous or subcutaneous administration to human beings. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing an anti-ANGPT2 antibody or an antigen-binding fragment thereof in lyophilized form and (b) a second container containing a pharmaceutically acceptable diluent (e.g., sterile water) for injection. The pharmaceutically acceptable diluent can be used for reconstitution or dilution of the lyophilized anti-ANGPT2 antibody or antigen-binding fragment thereof. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the anti-ANGPT2 antibody or antigen-binding fragment thereof that is effective in the treatment or prevention an ANGPT2 related diseases or disorders can be determined by standard clinical techniques. In addition, in vitro assays may optionally be employed to help identify optimal dosage ranges. The precise dose to be employed in the formulation will also depend on the route of administration, and the stage of disorder, and should be decided according to the judgment of the practitioner and each patient's circumstances. Effective doses may be extrapolated from dose-response curves derived from in vitro or animal model test systems.

For example, toxicity and therapeutic efficacy of the anti-ANGPT2 antibody or antigen-binding fragment thereof can be determined in cell cultures or experimental animals by standard pharmaceutical procedures for determining the $ED_{50}$ (the dose therapeutically effective in 50% of the population). An anti-ANGPT2 antibody or antigen-binding fragment thereof that exhibits a large therapeutic index is preferred.

The data obtained from the cell culture assays and animal studies can be used in formulating a range of dosage for use in humans. The dosage of the anti-ANGPT2 antibody or antigen-binding fragment thereof typically lies within a range of circulating concentrations that include the $ED_{50}$ with little or no toxicity. The dosage may vary within this range depending upon the dosage form employed and the route of administration utilized. For any anti-ANGPT2 antibody or antigen-binding fragment thereof used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography, ELISA and the like.

For intravitreal injection of the ANGPT2-antibody generally longer intervals between treatments are preferred. Due to its improved potency the ANGPT2 antibodies of the present invention can be administered in longer intervals.

In one embodiment, the ANGPT2-antibody is administered every 6 weeks, or every 7 weeks, or every 8 weeks, or every 9 weeks, or every 10 weeks, or every 11 weeks, or every 12 weeks. In a further embodiment, the ANGPT2-antibody of the invention is administered once every 3 months.

Antibodies of the present invention can be formulated to doses which include, but are not limited from 20 mg/ml to 180 mg/ml; or 20 mg/ml, 30 mg/ml, 40 mg/ml, 50 mg/ml, 60 mg/ml, 70 mg/ml, 80 mg/ml, 90 mg/ml, or 100 mg/ml. Preferably, antibodies of the present invention can be formulated in a liquid formulation of about 50 mg/ml to of about 150 mg/ml.

In some embodiments, the pharmaceutical compositions comprising the anti-ANGPT2 antibody or antigen-binding fragment thereof can further comprise a therapeutic agent, either conjugated or unconjugated to the binding agent.

Such combination therapy administration can have an additive or synergistic effect on disease parameters (e.g., severity of a symptom, the number of symptoms, or frequency of relapse).

With respect to therapeutic regimens for combinatorial administration, in a specific embodiment, an anti-ANGPT2 antibody or antigen-binding fragment thereof is administered concurrently with a therapeutic agent. In another specific embodiment, the therapeutic agent is administered prior or subsequent to administration of the anti-ANGPT2 antibody or antigen-binding fragment thereof, by at least an hour and up to several months, for example at least an hour, five hours, 12 hours, a day, a week, a month, or three months, prior or subsequent to administration of the anti-ANGPT2 antibody or antigen-binding fragment thereof.

The compounds of the invention may be used alone or in combination of one or more additional therapeutic agents. Nonlimiting examples of additional therapeutic agents may include:

antidiabetics such as alpha-glucosidase inhibitors (e.g., miglitol and acarbose), amylin analogs (e.g., pramlintide), dipeptidyl peptidase 4 inhibitors (e.g., alogliptin, sitagliptin, saxagliptin, and linagliptin), incretin mimetics (e.g., liraglutide, exenatide, liraglutide, exenatide, dulaglutide, albiglutide, and lixisenatide), insulin, meglitinides (e.g., repaglinide and nateglinide), biguanides (e.g., metformin); SGLT-2 inhibitors (e.g., canagliflozin, empagliflozin, and dapagliflozin), sulfonylureas (e.g., chlorpropamide, glimepiride, glyburide, glipizide, glyburide, tolazamide, and tolbutamide), and thiazolidinediones (e.g., rosiglitazone and pioglitazone);

angiotensin II receptor antagonists (angiotensin receptor blockers (ARBs)) such as candesartan, eprosartan, candesartan, irbesartan, losartan, olmesartan, telmisartan, valsartan, azilsartan, and medoxomil;

angiotensin converting enzyme inhibitors (e.g., benazepril, captopril, enalapril, fosinopril, lisinopril, moexipril, and perindopril);

anticoagulants (e.g. dabigatran, actylise, Warfarin, heparin, and acetylsalicylic acid);

bronchodilators including short-acting and long-action beta agonists (e.g., albuterol, levalbuterol, salmeterol, formoterol, arformoterol, vilanterol, indacaterol and olodaterol) and short- and long-acting anticholinergics (ipratropium, tiotropium, umeclidinium, glycopyrrolatei and aclidinium);

steroids such as fluticasone and budesonide;

antimalarials such as hydroxychloroquine or chloroquine;

virostatic nucleosid analogs such as remdesivir; and

HIV-protease inhibitors such as lopinavir-ritonavir;

Polynucleotides, Vectors, Host Cells, and Recombinant Methods

The present invention relates to isolated polynucleotides that comprise a sequence encoding an anti-ANGPT2 antibody, vectors, and host cells comprising the polynucleotides, and recombinant techniques for production of the antibody. The isolated polynucleotides can encode any desired form of the anti-ANGPT2 antibody including, for example, full length monoclonal antibodies, Fab, Fab', F(ab')$_2$, and Fv fragments, diabodies, linear antibodies, single-chain antibody molecules, and multispecific antibodies formed from antibody fragments.

The polynucleotide(s) that comprise a sequence encoding an anti-ANGPT2 antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The anti-ANGPT2 antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the anti-ANGPT2 antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the humanized anti-ANGPT2 antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-υ. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin. Common selectable markers for mammalian cells are those that enable the identification of cells competent to take up a nucleic acid encoding a humanized anti-ANGPT2 antibody, such as DHFR (dihydrofolate reductase), thymidine kinase, metallothionein-I and -II (such as primate metallothionein genes), adenosine deaminase, ornithine decarboxylase, and the like. Cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., DG44).

Alternatively, host cells (particularly wild-type hosts that contain endogenous DHFR) transformed or co-transformed with DNA sequences encoding anti-ANGPT2 antibody, wild-type DHFR protein, and another selectable marker such as aminoglycoside 3'-phosphotransferase (APH), can be selected by cell growth in medium containing a selection agent for the selectable marker such as an aminoglycosidic antibiotic, e.g., kanamycin, neomycin, or G418. See, e.g., U.S. Pat. No. 4,965,199.

Where the recombinant production is performed in a yeast cell as a host cell, the TRP1 gene present in the yeast plasmid YRp7 (Stinchcomb et al., 1979, Nature 282: 39) can be used as a selectable marker. The TRP1 gene provides a selection marker for a mutant strain of yeast lacking the ability to grow in tryptophan, for example, ATCC No. 44076 or PEP4-1 (Jones, 1977, Genetics 85:12). The presence of the trp1 lesion in the yeast host cell genome then provides an effective environment for detecting transformation by growth in the absence of tryptophan. Similarly, Leu2p-deficient yeast strains such as ATCC 20,622 and 38,626 are complemented by known plasmids bearing the LEU2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* (Van den Berg, 1990, Bio/Technology 8:135). Stable multi-copy expression vectors for secretion of mature recombinant human serum albumin by industrial strains of *Kluyveromyces* have also been disclosed (Fleer et al., 1991, Bio/Technology 9:968-975).

Expression and cloning vectors usually contain a promoter that is recognized by the host organism and is operably linked to the nucleic acid molecule encoding an anti-ANGPT2 antibody or polypeptide chain thereof. Promoters suitable for use with prokaryotic hosts include phoA promoter, β-lactamase and lactose promoter systems, alkaline phosphatase, tryptophan (trp) promoter system, and hybrid promoters such as the tac promoter. Other known bacterial promoters are also suitable. Promoters for use in bacterial systems also will contain a Shine-Dalgarno (S.D.) sequence operably linked to the DNA encoding the humanized anti-ANGPT2 antibody.

Many eukaryotic promoter sequences are known. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Inducible promoters have the additional advantage of transcription controlled by growth conditions. These include yeast promoter regions for alcohol dehydrogenase 2, isocytochrome C, acid phosphatase, derivative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-ANGPT2 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., 1982, Nature 297:598-601, disclosing expression of human p-interferon cDNA in mouse cells under the control of a thymidine kinase promoter from herpes simplex virus. Alternatively, the rous sarcoma virus long terminal repeat can be used as the promoter.

Another useful element that can be used in a recombinant expression vector is an enhancer sequence, which is used to increase the transcription of a DNA encoding an anti-ANGPT2 antibody by higher eukaryotes. Many enhancer sequences are now known from mammalian genes (e.g., globin, elastase, albumin, α-fetoprotein, and insulin). Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, Nature 297:17-18 for a description of enhancing elements for activation of eukaryotic promoters. The enhancer may be spliced into the vector at a position 5' or 3' to the anti-ANGPT2 antibody-encoding sequence, but is preferably located at a site 5' from the promoter.

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-ANGPT2 antibody. One useful transcription termination component is the bovine growth hormone polyadenylation region. See WO94/11026 and the expression vector disclosed therein. In some embodiments, anti-ANGPT2 antibodies can be expressed using the CHEF system. (See, e.g., U.S. Pat. No. 5,888,809; the disclosure of which is incorporated by reference herein.)

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-ANGPT2 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans,* and *K. marxianus; yarrowia* (EP 402,226); *Pichia* pastors (EP 183,070); *Candida; Trichoderma* reesia (EP 244,234); *Neurospora crassa; Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger*.

Suitable host cells for the expression of glycosylated anti-ANGPT2 antibody are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, *petunia*, tomato, and tobacco can also be utilized as hosts.

The inventive anti-ANGPT2 antibodies or antigen-binding fragments thereof can also be incorporated in viral vectors, i.e. the polynucleotide encoding for the anti-ANGPT2 antibody or antigen-binding fragment thereof is introduced into the viral vector and then expressed in the body of the patient after infection with the virus.

In another aspect, expression of anti-ANGPT2 is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/-DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Host cells are transformed with the above-described expression or cloning vectors for anti-ANGPT2 antibody production and cultured in conventional nutrient media modified as appropriate for inducing promoters, selecting transformants, or amplifying the genes encoding the desired sequences.

The host cells used to produce anti-ANGPT2 antibody described herein may be cultured in a variety of media. Commercially available media such as Ham's F10 (Sigma-Aldrich Co., St. Louis, Mo.), Minimal Essential Medium ((MEM), (Sigma-Aldrich Co.), RPMI-1640 (Sigma-Aldrich Co.), and Dulbecco's Modified Eagle's Medium ((DMEM), Sigma-Aldrich Co.) are suitable for culturing the host cells. In addition, any of the media described in one or more of Ham et al., 1979, Meth. Enz. 58: 44, Barnes et al., 1980, Anal. Biochem. 102: 255, U.S. Pat. Nos. 4,767,704, 4,657, 866, 4,927,762, 4,560,655, 5,122,469, WO 90/103430, and WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, Bio/Technology 10:163-167 describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. A variety of methods can be used to isolate the antibody from the host cell.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode an ANGPT2-antibody or antibody fragment. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-ANGPT2 polypeptide (e.g., a heavy chain or light chain variable region), or its complement. Hybridizing nucleic acids of the type described herein can be used, for example, as a cloning probe, a primer, e.g., a PCR primer, or a diagnostic probe.

In one embodiment, the present invention relates to an isolated polynucleotide or polynucleotides comprising:
a sequence encoding a heavy chain as shown in SEQ ID NO: 31 or a heavy chain variable region as shown in SEQ ID NO: 3; and a sequence encoding a light chain as shown in SEQ ID NO. 32 or a light chain variable region as shown in SEQ ID NO: 8,
or
an isolated polynucleotide or polynucleotides comprising a sequence encoding a heavy chain as shown in SEQ ID NO: 33 or a heavy chain variable region as shown in SEQ ID NO: 4; and a sequence encoding a light chain as shown in SEQ ID NO. 34 or a light chain variable region as shown in SEQ ID NO: 9,
or
an isolated polynucleotide or polynucleotides comprising a sequence encoding a heavy chain as shown in SEQ ID NO: 35 or a heavy chain variable region as shown in SEQ ID NO: 5; and a sequence encoding a light chain as shown in SEQ ID NO. 36 or a light chain variable region as shown in SEQ ID NO: 10,
or
an isolated polynucleotide or polynucleotides comprising a sequence encoding a heavy chain as shown in SEQ ID NO: 37 or a heavy chain variable region as shown in SEQ ID NO: 6; and a sequence encoding a light chain as shown in SEQ ID NO. 38 or a light chain variable region as shown in SEQ ID NO: 11,
or
an isolated polynucleotide or polynucleotides comprising a sequence encoding a heavy chain as shown in SEQ ID NO: 39 or a heavy chain variable region as shown in SEQ ID NO: 7; and a sequence encoding a light chain as shown in SEQ ID NO. 40 or a light chain variable region as shown in SEQ ID NO: 12.

It is to be understood that in said anti-ANGPT2 antibodies and antibody fragments the nucleic acid sequence coding for the CDRs remain unchanged (unchanged with respect to the amino acid they encode, equivalents of the DNA sequence due to the degeneracy of codons are possible) but the surrounding regions e.g. FR regions can be engineered.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the anti-ANGPT2 antibody or the antigen-binding fragment thereof. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

The invention is further described in the following examples, which are not intended to limit the scope of the invention.

EXAMPLES

Antibodies ANGPT2-opt-1, ANGPT2-opt-2, ANGPT2-opt-13, ANGPT2-opt-19, and ANGPT2-opt-31 are characterized along with comparator antibodies nesvacumab analog, MEDI3617 analog, and LC06. These comparator antibodies were produced using standard procedures based on published sequences as described below.

TABLE 4

Comparator anti-ANGPT2 antibodies.

| Comparator Antibody | Published sequence |
|---|---|
| Nesvacumab analog (Regeneron) Heavy chain: SEQ ID NO: 53 Light chain: SEQ ID NO: 54 | See the United States Adopted Name (USAN) file number ZZ-34 (2012) for nesvacumab. For the nesvacumab analog described here, the lysine residue at position 219 in the heavy chain of nesvacumab is replaced with arginine (K219R). |
| MEDI3617 analog (Medimmune) Heavy chain: SEQ ID NO: 55 Light chain: SEQ ID NO: 56 | The structure of the MEDI3617 analog used herein is based on the description in U.S. Pat. No. 8,507,656. |
| LC06 (Roche) Heavy chain: SEQ ID NO: 57 Light chain: SEQ ID NO: 58 | The structure of LC06 used herein is based on the description in U.S. Pat. No. 9,340,609. |

Data for these antibodies are described below.

Example 1: Antibody Generation (Immunization)

Wild type CD1 mice are immunized with recombinant human and murine ANGPT2 DNA, as well as human and murine ANGPT2 protein. Complete Freund's Adjuvant, Freund's Incomplete Adjuvant, Titermax, or Gerbu are used as adjuvants at various points to augment antibody responses. Serology is then assessed by ELISA. Selected serologically positive mice are given a final boost before B-cell isolation. The mice selected all exhibit positive antibody titers in the sera. At the end of the immunization regimen, splenocytes are harvested for recovery of antigen-specific B-cells.

Example 2. Production of Humanized Antibodies

The chimeric lead CL-209881_VL was selected for further optimization. The chimeric lead has a variable light chain corresponding to SEQ ID NO: 2 and a variable heavy chain corresponding to SEQ ID NO: 1. Thirty-three sequences (leads) were selected and optimized. Subsequent studies to the selection of six antibodies for further scale up.

Example 3. Sequence Liabilities in the CDRs

Sequences of the CDRs are checked for the presence for any potential liabilities such as N-glycosylation sites, strong Deamidation motifs (NG, NS, NH, NA, ND, NT, NN), Aspartate isomerization motifs (DG), Fragmentation motifs (DG, DS), Cysteine. These amino acids or motifs can undergo chemical reaction and confer undesired heterogeneity to the product, also with the possibility of negatively impacting target binding and function. For these reasons, it is preferred to remove such amino acids or motifs (if any) from the CDRs.

Example 4. Immunogenicity

Immunogenicity of sequences is evaluated in silico with an algorithm provided through a license company EpiVax, Inc., Providence, R.I. EpiMatrix Treg-adj Score take into consideration T cell epitopes and Treg epitopes. The lower the immunogenicity score, the less likely a sequence will be immunogenic. In general, a negative score is considered low risk of immunogenicity, while a positive score is viewed as indication for potential immunogenicity.

Example 5. Epitope Information

Materials
Water (Sigma Aldrich, P/N 37877-4L)
Acetonitrile (Sigma Aldrich, P/N 34998-4L)
Formic acid (Fluka, P/N 94318)
Urea (Sigma Aldrich, P/N 51456-500G)
TCEP-HCl—10 g (Thermo Scientific—Pierce, P/N 20491)
Sodium Phosphate Disbasic (Sigma Aldrich, P/N S7907-100G)
Sodium Phosphate Monobasic (Sigma Aldrich, P/N S8282-500G)
ACQUITY UPLC BEH C18 VanGuard Pre-column, 130 Å, 1.7 µm, 2.1 mm×5 mm (Waters Technologies Corp, 186003975)
Poroszyme® Immobilized Pepsin Cartridge, 2.1 mm×30 mm (Life Technologies Corp, 2313100)
Acquity UPLC BEH C18 Column 1.7 um, 1 mm×50 mm (Waters, 186002344)
Solvent A: 0.1% Formic acid/99% water/1% acetonitrile
Solvent B: 0.1% Formic acid/5% water/95% acetonitrile
Water Buffer: H2O 10 mM sodium phosphate pH 7.4
Deuterium Buffer: D2O 10 mM sodium phosphate pH 7.4
Quench Buffer: Water 8 M Urea, 0.4M TCEP-HCl In epitope mapping control samples, the antigen is run with and without antibody. To determine the list of antigen peptides, this protocol is first run using Water buffer in place of Deuterium buffer. 4 µL of sample is mixed with 40 µL of Deuterium buffer. This mixture is incubated at 20° C. for multiple time points (1, 2, and 4 minutes). Then 40 µL of the mixture is transferred to 40 µL of 4° C. quench buffer (4M Urea, 0.4M Tcep-HCl) and mixed. 60 µL of the quenched protein is injected, where it's digested on the pepsin column for 2 minutes by flowing 200 µL/mL of solvent A: 0.1% Formic acid/99% water/1% acetonitrile. The subsequent peptides are desalted on the Vanguard Pre-column for 3 minutes. The peptic peptides are sent to a BEH C18 reversed phase column inside the column/valve temperature controlled compartment. A gradient solvent system consisting of solvent A: 0.1% Formic acid/99% water/1% acetonitrile and solvent B: 0.1% Formic acid/5% water/95% acetonitrile is utilized. The percentage of solvent B is increased from 10% to 15% at 5.1 minute, to 50% at 11 minutes, to 90% at 11.5 minutes held to 12.5 minutes, to 0% B at 13 minutes held to 14 minutes. The chromatographic separation took place at 4° C. at a flow rate of 180 µl/min. After chromatographic separation, the sample enters the Thermo Scientific Orbitrap Fusion mass spectrometer operated in positive electrospray ionization mode. The employed method includes activation types of CID and ETD when identifying control peptides, utilizing a resolution of 120,000, a minimum signal of 10,000, an isolation width of 1.0 and a normalized collision energy of 35.0 V. The S-lens RF level is set at 60%. For control peptides, data collection type is profile for the full MS scan and centroid for the CID MS/MS data. For Deuterated samples, no MS/MS is collected. Data is collected over a mass range of 280-1800 Da. For raw LC-MS/MS fragmentation data analysis, control samples (with CID and ETD MS/MS) are analyzed using Proteome Discover 1.4 (Thermo Scientific) and PMi Byonic (Protein Metrics) against the given sequence to generate a list of peptides and retention times. Raw data files are preprocessed and converted to ASCII format using proprietary in-house SHARC software. Identified peptides are then matched and summarized using proprietary in-house SHAFT software. Epitopes are determined by differences in average mass shift induced by binding after Deuterium labeling. On a peptide level, protection greater than 0.4 Da is considered significant.

Results of the epitope mapping are shown for an exemplary antibody of the invention (ANGPT2-opt-13) (FIG. 2), the nesvacumab analog, the MED3617 analog and LC06. Nesvacumab reportedly does not cross-react with ANGPT1, whereas the MED3617 analog and LC06 reportedly cross-react with ANGPT1. Specific binding sites of the antibodies to the FLD domain of human ANGPT2 with SEQ ID NO: 50 (FIG. 2) are highlighted in dark grey. The data show that the comparator antibodies (nesvacumab analog, MED3617, and LC06) bind to epitopes that are different and distinct from the binding epitope of ANGPT2-opt-13.

Example 6. CDC Assay

The IgG heavy chain Fc region confers antibody effector functions through interaction with C1q and therefore may have the ability to induce complement-dependent cytotoxicity (CDC). This effect can be investigated in vitro by exposing target cells to complement in the presence of an antibody that specifically binds to the target cell. The CDC assay can be used to assess the activity of monoclonal antibodies to mediate CDC. (See "Mapping of the C1q binding site on Rituxan, a chimeric antibody with a human IgG1 Fc," Idusogie, Esohe E. et al., Journal of Immunology (2000), 164 (8), 4178-4184; and "Utilization of Complement-Dependent Cytotoxicity To Measure Low Levels of Antibodies: Application to Nonstructural Protein 1 in a Model of Japanese Encephalitis Virus," Konishi, Eiji et al., Clin Vaccine Immunol. (2008) January; 15(1): 88-94.)

CHO cells expressing membrane-bound human ANGPT2 (CHO-GPI-ANGPT2) are cultured in RPMI-1640 with the addition of HI FBS, 1× glutamax, and 1000 µg/ml Geneticin (used as target cells). CDC activity is determined by measuring release of LDH from target cells using the Cytotoxicity Detection Kit Plus from Roche®. Samples are set up in triplicate in 96-well round bottom plates. Samples consist of 50 µl antibody, 50 µl target cells (50,000/well), and 100 µl human complement (Cedarlane®), at 1:12 final dilution in cytotoxicity media (Cedarlane®). Background control is 200 µl cytotoxicity media (Cedarlane®) only. Maximal release control (Tmax) is 50 µl target cells and 150 µl cytotoxicity media. Target cell control (Tspon) is 50 µl target cells and 150 µl cytotoxicity media. The plate is incubated at 37° C. in a humid $CO_2$ incubator for 3 hours. Thirty minutes before the end of the incubation (after 2.5 hrs incubation), 10 µl Lysis Solution (provided in the Cytotoxicity Detection Kit-Roche®) is added to the maximal release (Tmax) control wells. At the end of the incubation, 100 µl of the supernatants are transferred into corresponding wells of a 96-well flat-bottom plate for LDH detection. 100 µl of Reaction mixture (provided in the Cytotoxicity Detection Kit) is added to each well and the plate is incubated at room temperature for 15 min in the dark. At the end of this second incubation, the reaction is stopped by adding 50 µl of Stop solution (provided in the Cytotoxicity Detection Kit). The absorbance is measured at a wavelength of 490 nm with 650 nm as reference on Biotek® plate reader (Biotek, Synergy). CDC % is calculated using the equation:

$$\% \text{ CDC} = ((\text{Ab induced release}) - [(T)\_\text{spon}]) / ((T\_\text{max}) - (T\_\text{spon})) * 100$$

Figure 1B:
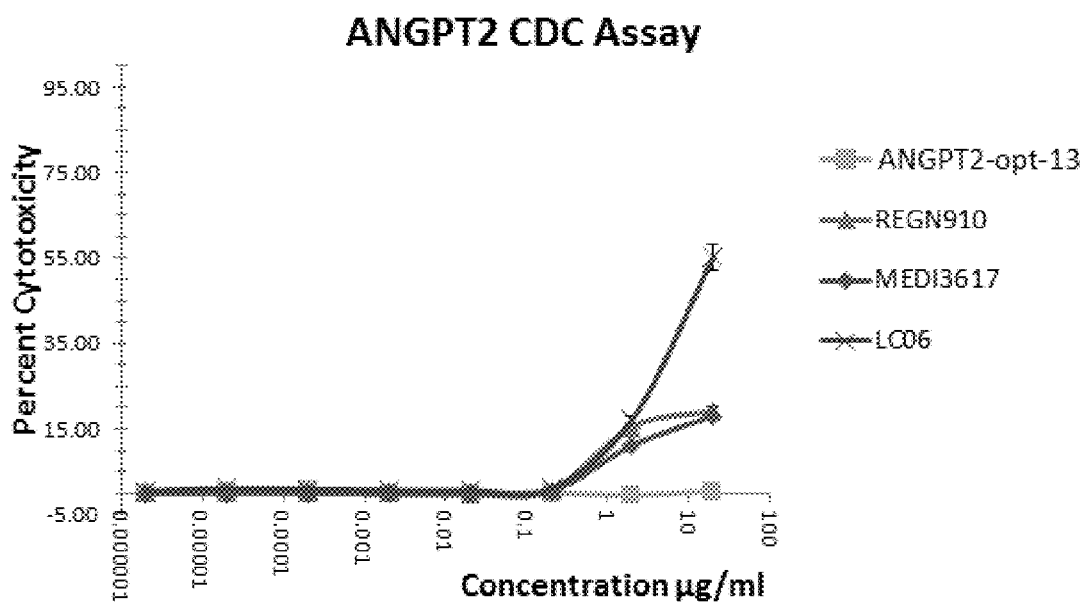
Figure 3A:
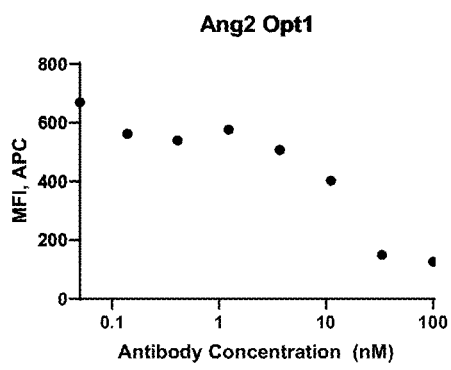
FIGS. 3A-3F shows results for an ANGPT2 blocking assay for ANGPT2-opt-1) (FIG. 3A), ANGPT2-opt-2 (FIG. 3B), ANGPT2-opt-13 (FIG. 3C), ANGPT2-opt-19 (FIG. 3D), ANGPT2-opt-31 (FIG. 3E), chimeric lead CL-209881 (FIG. 3F), and an analog of nesvacumab (FIG. 3G).
Figure 3B:
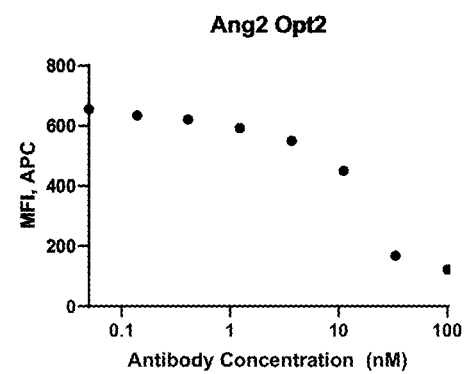
Figure 3C:
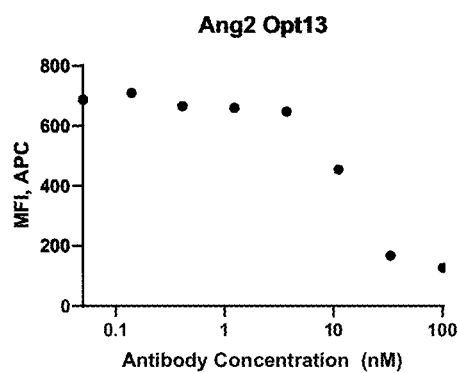
Figure 3D:
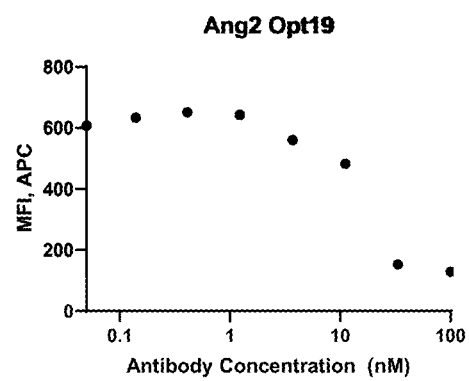
Figure 3E:
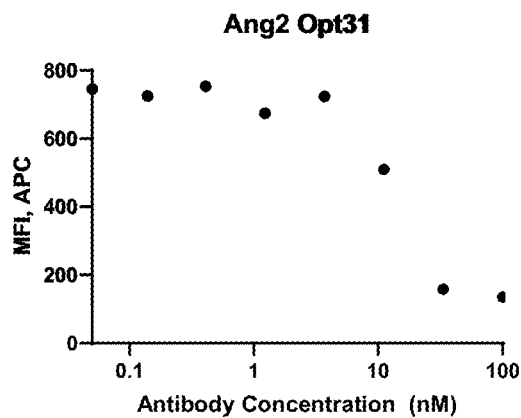
Figure 3F:
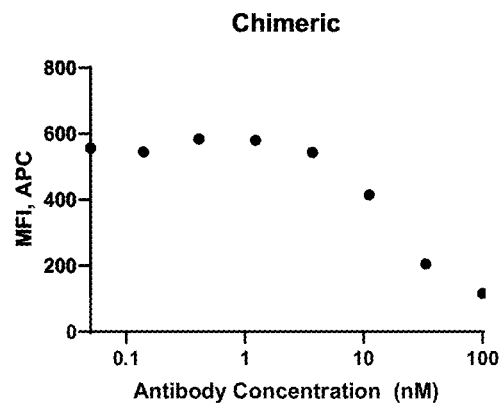
Figure 3G:
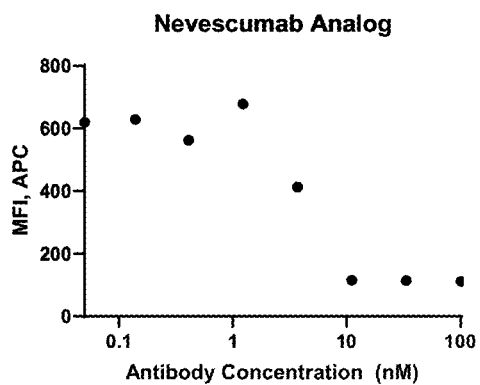

The above-described CDC study is used to determine the cytotoxicites results of anti-ANG antibodies: ANGPT2-opt-13-IgG, nesvacumab analog, MED3617 analog, and LC06. The results of duplicate studies are shown in FIGS. 1A and 1B. The results show that the exemplary anti-ANGPT2 antibody of the invention (ANGPT2-opt-13-IgG) is less cytotoxic than each of the nesvacumab analog, the MEDI3617 analog, and LC06.

Example 7. ANGPT2 Blocking Assay

Human ANGPT2 Dimer (CC-FLD) is pre-incubated with the testing antibodies. The ANGPT2/Antibody mixture is then incubated with HEK293 human Tie2 cells at 4° C. After washing, the cells are stained with anti-His-AF647 (from GenScript) for detection of the His-tag on the ANGPT2 protein. The binding of the secondarily labelled ANGPT2 to human Tie2 cells is detected by FLOW cytometry. The average of the duplicate values for each concentration point is used to derive the curve fit graphs. Antibodies that prevent ANGPT2 from binding to the Tie2 cells are considered blocking antibodies. The results are shown in FIGS. 3A-3G and the EC50 values are shown in Table 5 based on the average of duplicate values.

TABLE 5

| ANGPT2 blocking assay. | |
|---|---|
| Anti-ANGPT2 antibody | EC50, nM |
| Ang2-opt-1 | 13.22 |
| Ang2-opt-2 | 14.81 |
| Ang2-opt-13 | 12.98 |
| Ang2-opt-19 | 15.08 |
| Ang2-opt-31 | 13.03 |
| Nevescumab analog | 3.77 |

The results of the ANGPT2 blocking assay show antibodies of the invention block ANGPT2 interaction with the receptor Tie2 on the cell surface.

Example 8. Tie2 Phosphorylation Functional Assay

The Tie2 phosphorylation functional assay is carried out as described below.

Unless otherwise indicated, the following reagents or materials are used:

HEK293/huTie2 cells;
0.25% trypsin/EDTA (Gibco cat. #25200-056);
Poly-D-lysine coated black, clear bottom 96 well/plate (BioCoat cat #35460);
PathScan Sandwich ELISA lysis Buffer (Cell Signaling, cat #7018);
HALT protease and phosphatase inhibitor cocktail (Thermo Scientific, cat. #78443, lot #QK226996, 100× stock);
Activated sodium orthovanadate, 200 mM stock (Five photon, cat. #ActVO-4, lot #26716-4);
Clear 96 well high bind polystyrene microplates (R&D Systems cat. #DY990, lot #316940);
ELISA blocking buffer: Phosphate Buffered Saline (PBS) w/2% BSA, diluted from 10% stock (R&D Systems, cat #DY995);
ELISA assay diluent: PBS w/1% BSA, diluted from 10% stock (R&D Systems, cat #DY995);
ELISA wash buffer concentrate: 25× stock (R&D Systems, cat. #WA126);
ELISA substrate reagent pack (R&D Systems, catDY999);
ELISA stop solution (R&D Systems, cat DY994); and
rhAngiopoietin-2 (R&D systems cat623-AN/CF; lot #SUL61 at 169 ug/ml stock).

Cell-Plating Medium:
Dulbecco's Modified Eagle Medium (DMEM) with 4.5 g/l Glucose with L-Glutamine (500 ml) (Gibco cat. #11995-065);
Fetal Bovine Serum (FBS) (50 ml) (Hyclone cat SH30071.03, Lot #AC10219630);
100 mM Non-Essential Amino Acids (NEAA) Solution (5 ml) (Gibco: cat. #11140-050);
100 mM Sodium Pyruvate (5 ml) (Gibco cat #11360-070);
PenStrep (5 ml) (Gibco cat. #15140-122); and
1M N-2-hydroxyethylpiperazine-N-2-ethane sulfonic acid (Hepes) (6.25 ml) (Gibco cat. #15630-080); Geneticin (10 ml) (Gibco cat #10131-035).

Starving Media:
DMEM with 4.5 g/l Glucose with L-Glutamine;
FBS (25 ml) 5%; NEAA (5 ml);
Sodium Pyruvate (5 ml); PenStrep (2.5 ml);
Hepes (6.25 ml); and
Geneticin (10 ml) Dulbecco's Phosphate-Buffered Saline (dPBS), calcium and magnesium free (Gibco cat. #14190).

Cell Plating

HEK293/huTie2 cells are washed with PBS, detached with 0.25% Trypsin, and counted using a countess cell counter (Invitrogen). $5 \times 10^4$ cells are plated per well in a 96 well Ploy D-Lysine clear bottom tissue culture plate in 100 ul Dulbecco's Modified Eagle Medium (DMEM) with 10% FBS, NEAA, Sodium Pyruvate, PenStrep, Geneticin and HEPES. The cells are incubated overnight at 37° C., 5% $CO_2$ incubator. After about 18 hours, the cell-plating media is replaced with 100 ul of starving media (Dulbecco's Modified Eagle Medium (DMEM) with 5% FBS, NEAA, Sodium Pyruvate, PenStrep, Geneticin and HEPES, returned the plate to incubator, and incubated overnight.

ELISA Plate Coating

The capture antibody (antiTie2 (AB33) from Cell signalling) is diluted to a 1 ug/ml working solution in coating buffer (eBioscience). The working solution is immediately added to a 96 well high binding polystyrene microplate (R&D) to provide 100 ul per well. The wells are seal plated and incubated overnight at 4° C. The plate is washed 3 times with 300 ul per well by 1×ELISA wash buffer and then blocked with 200 ul blocking buffer for 2 hr at room temperature while shaking.

Cell Treatment

A stock solution of Ang2 (rhAngiopoietin-2 from R&D systems catalog #623-AN/CF; lot #SUL61) is diluted to 6 ug/ml in starving media. (The starving media is also used as antibody diluent.) Separately, solutions of the anti-ANGPT2 antibodies are prepared by dilution to 66 nM followed by 1:3 serial dilution to 0.27 nM. Anti-ANGPT2 antibodies with rhAng2 are incubated at room temperature for 30 min. Cell culture media (50 ul) is removed from each well in cell plate. The cells are treated with 50 ul aliquots of the preincubated anti-ANGPT2 antibody solution for 20 minutes at 37° C., 5% $CO_2$ incubator. The supernatant is discarded and the cells are washed once with cold PBS (containing 1 mM activated sodium orthovanadate). The wash buffer is discarded and PathScan lysis buffer (cell signaling) with 1 mM activated sodium orthovanadate, protease and phosphatase inhibitors) is added to each cell. The plate is shaken at rapid speed for 1-3 hr at 4° C.

ELISA

The blocking buffer is removed from the ELISA plate, cell lysate is added to each well, and the plate is incubated overnight at 4° C. with shaking. The plate is washed four times with ELISA wash buffer, and each well is treated with detection antibody: Biotin Conjugate-4G10 platinum anti-Phospotyrosine (from Millipore) at 1:300 dilution in ELISA assay diluent. The plate is incubated for 2 hr on the shaker at room temperature and then washed four times with ELISA wash buffer. Streptavidin-HRP conjugated (from Millipore) diluted at 1:300 in ELISA assay diluent is added to each well and incubated on a shaker for 1 hr at room temperature. The plate is washed four times with ELISA wash buffer. Following the wash step, substrate solution from ELISA substrate reagent pack (R&D Systems) is added to each well at room temperature for 5-10 min. Stop solution is added followed by gentle tapping for 5 minutes to ensure thorough mixing. The plate is then read with a plate reader with absorbance at 450 nm corrected with 650 nm.

TABLE 6

Tie2 phosphorylation functional assay.

| Anti-ANGPT2 antibody | EC50, nM | EC50, nM |
| --- | --- | --- |
| Ang2-opt-1 | 3.0 | 3.2 |
| Ang2-opt-2 | 1.8 | 1.9 |
| Ang2-opt-13 | 4.2 | 4.0 |
| Ang2-opt-19 | 5.0 | 4.6 |
| Ang2-opt-31 | 4.4 | 3.8 |
| Ang2-opt-34 | 5.8 | 7.4 |
| Nevescumab analog | 4.4 | 2.2 |
| MEDI3617 analog | — | 2.7 |
| LC06 | 1.3 | — |

The results of the Tie2 functional assay show that the anti-ANGPT2 antibodies inhibit ANGPT2-induced Tie2 phosphorylation and can block Tie2-mediated phosphorylation and downstream signalling.

Example 9. Binding Affinity

The binding affinity to the various ANGPT2 analytes is determined by surface plasmon resonance (SPR) using a ProteOn XPR36 (Bio-Rad). Unless otherwise stated, all reagents are obtained from Bio-Rad. The running buffer for all assays and dilutions (except where stated) is phosphate buffered saline (PBS)/ethylenediamine tetraacetic acid (EDTA) with 0.01% Tween20 (PBS-T-EDTA). PBS-T-EDTA is prepared by adding 100 µl of 100% Tween20 to 2 L of PBS-T-EDTA with an initial concentration of 0.005% Tween20 to make a final Tween20 concentration of 0.01%. The general linearized model (GLM) sensorchip is normalized, pre-conditioned, and activated with an equal mixture of 1-ethyl-3-[3-dimethylaminopropyl]carbodiimide (EDC)/N-hydroxysulfosuccinimide (s-NHS) in the horizontal direction for 300 sec at a flow rate of 30 µl/min. Immobilization is then is done with Recombinant Protein A/G (Thermo Scientific) (60 µg/ml in 10 mM acetate pH 4.5) in the horizontal direction for 300 sec at a flowrate of 30 µl/min resulting in about 4370-4875 response units (RUs) of Protein A/G on the surface. The sensorchip is then deactivated with 1M ethanolamine HCl in the horizontal direction for 300 sec at a flowrate of 30 µl/min. The sensorchip is stabilized with 18 sec of 0.85% phosphoric acid at a flowrate of 100 µl/min 3 times horizontally and 3 times vertically.

Each ANGPT2 antibody is captured on the Protein A/G surface vertically for 300 sec at a flowrate of 30 µl/min resulting in a capture level of about 2500 RU. The baseline is stabilized by injecting PBS-T-EDTA for 60 sec at a flowrate of 100 µl/min horizontally with dissociation of 120 sec. The analyte (e.g., HuANGPT2) is injected horizontally over the captured antibody for 300 sec at a flowrate of 30 µl/min and a dissociation for 1800 sec. The concentrations of the analytes are 0 nM, 6.25 nM, 12.5 nM, 25 nM, 50 nM, and 100 nM. The surface is regenerated by injecting 0.85% phosphoric acid for 18 sec at a flowrate of 100 µl/min one time horizontally and one time vertically. PBS-T-EDTA is injected for 60 sec at a flowrate of 100 µl/min one time vertically and one time horizontally.

The interspot (interactions with sensor surface) and blank (PBS-T-EDTA with 0.01% Tween20 or 0 nM of analyte (here HuANGPT2)) are subtracted from the raw data. Sensorgrams are then fit to 1:1 Langmuir binding to provide on-rate ($k_a$), off-rate ($k_d$), and affinity ($K_D$) values.

The above procedure is used to measure the binding affinity to the following analytes: human ANGPT1, human ANGPT2, cynomolgus (cyno) ANGPT2, rabbit ANGPT2, and rat ANGPT2. For the anti-ANGPT2 antibodies of the invention and the nesvacumab analog, no binding is observed in human ANGPT1 ($K_D$>100 nM). The results for binding to human ANGPT2 and cyno ANGPT2 are shown in Table 7.

TABLE 7

Affinity binding properties of antibodies to ANGPT2 in human and cyno models.

| | human ANGPT2 | | | cyno ANGPT2 | | |
|---|---|---|---|---|---|---|
| Antibody | $k_a$(1/Ms) | $k_d$ (1/s) | $K_D$ (nM) | $k_a$(1/Ms) | $k_d$ (1/s) | $k_D$ (nM) |
| CL_209881 | 1.51E+05 | 2.34E−05 | 0.155 | 1.64E+05 | 3.93E−05 | 0.240 |
| ANGPT2-opt-1 | 1.44E+05 | 4.25E−05 | 0.294 | 1.52E+05 | 5.48E−05 | 0.360 |
| ANGPT2-opt-2 | 1.25E+05 | 8.11E−05 | 0.649 | 1.35E+05 | 8.45E−05 | 0.626 |
| ANGPT2-opt-13 | 1.32E+05 | 1.89E−05 | 0.144 | 1.42E+05 | 2.08E−05 | 0.146 |
| ANGPT2-opt-19 | 8.18E+04 | 5.83E−05 | 0.712 | 8.77E+04 | 7.40E−05 | 0.844 |
| ANGPT2-opt-31 | 1.25E+05 | 1.14E−05 | 0.091 | 1.35E+05 | 1.96E−05 | 0.145 |
| Nesvacumab analog | 1.48E+05 | 1.93E−05 | 0.130 | 1.51E+05 | 1.93E−05 | 0.128 |
| MEDI3617 analog | 6.14E+05 | 1.66E−02 | 27 | NA | NA | NA |
| LC06 | 1.05E+05 | 1.25E−02 | 12 | NA | NA | NA |

NA = not available/not measured

For studies carried out in the rabbit ANGPT2 model, ANGPT2-opt-13 and nesvacumab analog exhibit $K_D$ values of 0.133 nM and 0.137 nM, respectively.

For studies carried out in the rat model, the anti-ANGPT2 antibodies of the invention showed only weak binding ($K_D$≥118 nM), whereas the nesvacumab analog exhibits a $K_D$ value of 0.159 nM.

The results show that the anti-ANGPT2 antibodies of the invention have a high affinity for human ANGPT2 and no measurable affinity for human ANGPT1.

The current disclosure contains, inter alia, the following items:

EMBODIMENT 1

An anti-ANGPT2 antibody or an antigen-binding fragment comprising:
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 17 (H-CDR3), and
a light chain variable region comprising the amino acid sequence of SEQ ID NO. 19 (L-CDR1); the amino acid sequence of SEQ ID NO. 22 (L-CDR2); and the amino acid sequence of SEQ ID NO. 24 (L-CDR3),
or
a heavy chain variable region comprising the amino acid sequence of SEQ ID NO. 14 (H-CDR1); the amino acid sequence of SEQ ID NO. 15 (H-CDR2); and the amino acid sequence of SEQ ID NO. 17 (H-CDR3); and
a light chain variable region comprising the amino acid sequence of SEQ ID NO. 19 (L-CDR1); the amino acid sequence of SEQ ID NO. 22 (L-CDR2); and the amino acid sequence of SEQ ID NO. 24 (L-CDR3),
or a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 16 (H-CDR3); and
a light chain variable region comprising the amino acid sequence of SEQ ID NO. 20 (L-CDR1); the amino acid sequence of SEQ ID NO. 23 (L-CDR2); and the amino acid sequence of SEQ ID NO. 24 (L-CDR3),
or
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 16 (H-CDR3); and
a light chain variable region comprising the amino acid sequence of SEQ ID NO. 21 (L-CDR1); the amino acid sequence of SEQ ID NO. 23 (L-CDR2); and the amino acid sequence of SEQ ID NO. 25 (L-CDR3),
or
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 16 (H-CDR3); and
a light chain variable region comprising the amino acid sequence of SEQ ID NO. 20 (L-CDR1); the amino acid sequence of SEQ ID NO. 22 (L-CDR2); and the amino acid sequence of SEQ ID NO. 24 (L-CDR3).

EMBODIMENT 2

The anti-ANGPT2 antibody of embodiment 1, wherein said antibody comprises a variable heavy chain and a variable light chain comprising the amino acid sequences of SEQ ID NO. 3 and SEQ ID NO. 8, respectively; SEQ ID NO. 4 and SEQ ID NO. 9, respectively; SEQ ID NO. 5 and SEQ ID NO. 10, respectively; SEQ ID NO. 6 and SEQ ID NO. 11, respectively; or SEQ ID NO. 7 and SEQ ID NO. 12, respectively.

EMBODIMENT 3

The anti-ANGPT2 antibody of embodiment 2, wherein said antibody comprises a variable heavy chain and a variable light chain having at least 90%, at least 95%, at least 98%, or at least 99% identity to the amino acid sequences of SEQ ID NO. 3 and SEQ ID NO. 8, respectively; SEQ ID NO. 4 and SEQ ID NO. 9, respectively; SEQ ID NO. 5 and SEQ ID NO. 10, respectively; SEQ ID NO. 6 and SEQ ID NO. 11, respectively; or SEQ ID NO. 7 and SEQ ID NO. 12, respectively.

EMBODIMENT 4

The anti-ANGPT2 antibody of embodiment 1, wherein said antibody comprises a heavy chain and a light chain comprising SEQ ID NO. 31 and SEQ ID NO. 32, respectively; SEQ ID NO. 33 and SEQ ID NO. 34, respectively; SEQ ID NO. 35 and SEQ ID NO. 36; respectively; SEQ ID NO. 37 and SEQ ID NO. 38; respectively; or SEQ ID NO. 39 and SEQ ID NO. 40.

EMBODIMENT 5

The anti-ANGPT2 antibody of embodiment 4, wherein said antibody comprises a heavy chain and a light chain having at least 90%, at least 95%, at least 98%, or at least 99% identity to the amino acid sequences of SEQ ID NO. 31 and SEQ ID NO. 32, respectively; SEQ ID NO. 33 and SEQ ID NO. 34, respectively; SEQ ID NO. 35 and SEQ ID NO. 36; respectively; SEQ ID NO. 37 and SEQ ID NO. 38; respectively; or SEQ ID NO. 39 and SEQ ID NO. 40.

EMBODIMENT 6

The anti-ANGTP2 antibody or antigen-binding fragment thereof according to any of embodiments 1 to 5, wherein the anti-ANGTP2 antibody or antigen-binding fragment thereof that binds to at least one amino acid residue of SEQ ID NO: 51, or to SEQ ID NO: 51.

EMBODIMENT 7

An anti-ANGTP2 antibody or antigen-binding fragment thereof that binds to at least one amino acid residue within amino acid regions of the FLD domain of human ANGPT2 with the SEQ ID NO: 51, or to SEQ ID NO: 51.

EMBODIMENT 8

An anti-ANGTP2 antibody or antigen-binding fragment thereof that competes for binding to SEQ ID No: 51 with an anti-ANGTP2 antibody according to any of embodiments 1 to 7.

EMBODIMENT 9

An isolated polynucleotide having a sequence which encodes an antibody as defined in any of embodiments 1 to 8.

EMBODIMENT 10

A vector comprising the polynucleotide according to embodiment 9.

EMBODIMENT 11

A host cell transformed or transfected with the polynucleotide according to embodiment 9 or with the vector according to embodiment 10.

EMBODIMENT 12

A method for producing an antibody according to any of embodiments 1 to 8, comprising (a) culturing a host cell according to embodiment 11 under conditions allowing the expression of the antibody according to any of embodiments 1 to 8 and (b) recovering the produced antibody from the culture.

EMBODIMENT 13

A pharmaceutical composition comprising the anti-ANGPT2 antibody or the antigen-binding fragment according to any of embodiments 1 to 8, and a pharmaceutically acceptable carrier.

EMBODIMENT 14

The pharmaceutical composition according to embodiment 13, wherein the composition further comprises a second therapeutic agent selected.

EMBODIMENT 15

The pharmaceutical composition according to embodiment 13 or 14, wherein the composition is administered by a parenteral route, intravenous route or subcutaneous route of administration.

EMBODIMENT 16

An anti-ANGPT2 antibody or the antigen-binding fragment according to any of embodiments 1 to 8 for use as a medicament.

EMBODIMENT 17

A method of treating diseases or disorders that can be alleviated by treatment with an anti-ANGPT2 antibody, the method comprising administering to a patient in need thereof a pharmaceutically effective amount of the anti-ANGPT2 antibody or the antigen-binding fragment according to any one of embodiments 1 to 8.

EMBODIMENT 18

An anti-ANGPT2 antibody or the antigen-binding fragment according to any of embodiments 1 to 8 for use in treating diseases or disorders that can be alleviated by treatment with an anti-ANGPT2 antibody.

EMBODIMENT 19

Use of the anti-ANGPT2 antibody or the antigen-binding fragment according to any of claims 1 to 8 in manufacture of a medicament for treating diseases or disorders that can be alleviated by treatment with an anti-ANGPT2 antibody.

EMBODIMENT 20

The method of embodiment 17, the anti-ANGPT2 antibody or the antigen-binding fragment of embodiment 18, or the use of the anti-ANGPT2 antibody or the antigen-binding fragment of embodiment 19, wherein the disease or disorder is selected from the group consisting of cardiac hypertrophy, myocardial infarction, ischemia, ischemic reperfusion injury, stroke hypertension, pulmonary arterial hypertension, idiopathic pulmonary arterial hypertension, trauma induced brain disorders, asthma, chronic obstructive pulmonary disease (COPD), rheumatoid arthritis, inflammatory bowel disease, multiple sclerosis, -preeclampsia and pregnancy-induced hypertension, sepsis, severe sepsis, septic shock, non-alcoholic steatohepatitis (NASH), cirrhosis, minimal change disease, focal segmental glomerulosclerosis (FSGS), nephrotic syndrome, diabetic kidney disease (DKD), chronic kidney disease (CKD), diabetic renal insufficiency, end stage renal disease, ischemia or an ischemic reperfusion injury, cancer, hepatocellular carcinoma, idiopathic pulmonary fibrosis (IPF), emphysema, acute lung injury (ALI), acute respiratory disease syndrome (ARDS), severe acute respiratory syndrome (SARS), Middle Eastern respiratory syndrome (MERS), vascular hyperpermeability (and associated disorders), acute kidney injury, renal cell carcinoma, heart failure, lupus nephritis, Raynaud's, pancreatitis, peripheral artery disease, congenital heart disease, Dengue virus, malaria, hantavirus, edema, regeneration, lupus, interstitial lung disease, scleroderma, retinopathies, diabetic nephropathy, portal hypertension, varices growth, and liver transplantation

EMBODIMENT 21

The method of embodiment 20, the anti-ANGPT2 antibody or the antigen-binding fragment of embodiment 20, or the use of the anti-ANGPT2 antibody or the antigen-binding fragment of embodiment 20, wherein the disease or disorder is selected from the group consisting of chronic kidney disease, non-alcoholic steatohepatitis (NASH), and sepsis.

EMBODIMENT 22

The method of embodiment 17 or 20, further comprising administering a second therapeutic agent selected.

EMBODIMENT 23

The method of embodiment 17 or 20, wherein said antibody is administered by a parenteral route, intravenous route or subcutaneous route of administration.

EMBODIMENT 24

A method of blocking the function of human ANGPT2 in a human patient, comprising administering to said human patient a composition comprising the anti-ANGPT2 antibody or the antigen-binding fragment according to any of embodiments 1 to 8 in an amount sufficient to block an ANGPT2 mediated response in said human patient.

EMBODIMENT 25

An anti-ANGPT2 antibody or the antigen-binding fragment according to any of embodiments 1 to 8 for use in blocking the function of human ANGPT2.

EMBODIMENT 26

Use of the anti-ANGPT2 antibody or the antigen-binding fragment according to any of embodiments 1 to 8 in manufacture of a medicament for blocking the function of human ANGPT2.

EMBODIMENT 27

An isolated polynucleotide encoding a heavy chain variable region amino acid sequence or a light chain variable region, wherein the heavy chain variable region amino acid sequence comprises any of SEQ ID NOs: 3 to 7, SEQ ID NOs: 13 to 17; SEQ ID NO: 31, SEQ ID NO: 33, SEQ ID NO: 35, SEQ ID NO: 37, or SEQ ID NO: 39; a and the light chain variable region amino acid sequence comprises any of SEQ ID NOs: 8 to 12, SEQ ID NOs: 19 to 26, SEQ ID NO: 32, SEQ ID NO: 34, SEQ ID NO: 36, SEQ ID NO: 38, or SEQ ID NO: 40.

What is claimed is:

1. An anti-ANGPT2 antibody or an antigen-binding fragment comprising:
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 17 (H-CDR3), and
a light chain variable region comprising the amino acid sequence of SEQ ID NO. 19 (L-CDR1); the amino acid sequence of SEQ ID NO. 22 (L-CDR2); and the amino acid sequence of SEQ ID NO. 24 (L-CDR3),
or
a heavy chain variable region comprising the amino acid sequence of SEQ ID NO. 14 (H-CDR1); the amino acid sequence of SEQ ID NO. 15 (H-CDR2); and the amino acid sequence of SEQ ID NO. 17 (H-CDR3); and
a light chain variable region comprising the amino acid sequence of SEQ ID NO. 19 (L-CDR1); the amino acid sequence of SEQ ID NO. 22 (L-CDR2); and the amino acid sequence of SEQ ID NO. 24 (L-CDR3),
or
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 16 (H-CDR3); and
a light chain variable region comprising the amino acid sequence of SEQ ID NO. 20 (L-CDR1); the amino acid sequence of SEQ ID NO. 23 (L-CDR2); and the amino acid sequence of SEQ ID NO. 24 (L-CDR3),
or
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 16 (H-CDR3); and
a light chain variable region comprising the amino acid sequence of SEQ ID NO. 21 (L-CDR1); the amino acid sequence of SEQ ID NO. 23 (L-CDR2); and the amino acid sequence of SEQ ID NO. 25 (L-CDR3),
or
a heavy chain variable region comprising the amino acid sequence of SEQ ID NO. 13 (H-CDR1); the amino acid sequence of SEQ ID NO. 15 (H-CDR2); and the amino acid sequence of SEQ ID NO. 16 (H-CDR3); and
a light chain variable region comprising the amino acid sequence of SEQ ID NO. 20 (L-CDR1); the amino acid sequence of SEQ ID NO. 22 (L-CDR2); and the amino acid sequence of SEQ ID NO. 24 (L-CDR3).

2. The anti-ANGPT2 antibody of claim 1, wherein said antibody comprises a variable heavy chain and a variable light chain comprising the amino acid sequences of SEQ ID NO. 3 and SEQ ID NO. 8, respectively; SEQ ID NO. 4 and SEQ ID NO. 9, respectively; SEQ ID NO. 5 and SEQ ID NO. 10, respectively; SEQ ID NO. 6 and SEQ ID NO. 11, respectively; or SEQ ID NO. 7 and SEQ ID NO. 12, respectively.

3. The anti-ANGPT2 antibody of claim 1, wherein said antibody comprises a heavy chain and a light chain comprising SEQ ID NO. 31 and SEQ ID NO. 32, respectively; SEQ ID NO. 33 and SEQ ID NO. 34, respectively; SEQ ID NO. 35 and SEQ ID NO. 36; respectively; SEQ ID NO. 37 and SEQ ID NO. 38; respectively; or SEQ ID NO. 39 and SEQ ID NO. 40.

4. A pharmaceutical composition comprising the anti-ANGPT2 antibody or the antigen-binding fragment according to claim 1, and a pharmaceutically acceptable carrier.

5. The anti-ANGPT2 antibody or an antigen-binding fragment of claim 1, wherein the heavy chain variable region comprises the amino acid sequence of SEQ ID NO. 13 (H-CDR1); the amino acid sequence of SEQ ID NO. 15 (H-CDR2); and the amino acid sequence of SEQ ID NO. 17 (H-CDR3), and
the light chain variable region comprises the amino acid sequence of SEQ ID NO. 19 (L-CDR1); the amino acid sequence of SEQ ID NO. 22 (L-CDR2); and the amino acid sequence of SEQ ID NO. 24 (L-CDR3).

6. The anti-ANGPT2 antibody or an antigen-binding fragment of claim 1, wherein the heavy chain variable region comprises the amino acid sequence of SEQ ID NO. 14 (H-CDR1); the amino acid sequence of SEQ ID NO. 15 (H-CDR2); and the amino acid sequence of SEQ ID NO. 17 (H-CDR3); and
the light chain variable region comprises the amino acid sequence of SEQ ID NO. 19 (L-CDR1); the amino acid sequence of SEQ ID NO. 22 (L-CDR2); and the amino acid sequence of SEQ ID NO. 24 (L-CDR3).

7. The anti-ANGPT2 antibody or an antigen-binding fragment of claim 1, wherein the heavy chain variable region comprises the amino acid sequence of SEQ ID NO. 13 (H-CDR1); the amino acid sequence of SEQ ID NO. 15 (H-CDR2); and the amino acid sequence of SEQ ID NO. 16 (H-CDR3); and
the light chain variable region comprise the amino acid sequence of SEQ ID NO. 20 (L-CDR1); the amino acid sequence of SEQ ID NO. 23 (L-CDR2); and the amino acid sequence of SEQ ID NO. 24 (L-CDR3).

8. The anti-ANGPT2 antibody or an antigen-binding fragment of claim 1, wherein the heavy chain variable region comprises the amino acid sequence of SEQ ID NO. 13 (H-CDR1); the amino acid sequence of SEQ ID NO. 15 (H-CDR2); and the amino acid sequence of SEQ ID NO. 16 (H-CDR3); and
the light chain variable region comprises the amino acid sequence of SEQ ID NO. 21 (L-CDR1); the amino acid sequence of SEQ ID NO. 23 (L-CDR2); and the amino acid sequence of SEQ ID NO. 25 (L-CDR3).

9. The anti-ANGPT2 antibody or an antigen-binding fragment of claim 1, wherein the heavy chain variable region comprises the amino acid sequence of SEQ ID NO. 13 (H-CDR1); the amino acid sequence of SEQ ID NO. 15 (H-CDR2); and the amino acid sequence of SEQ ID NO. 16 (H-CDR3); and
the light chain variable region comprises the amino acid sequence of SEQ ID NO. 20 (L-CDR1); the amino acid sequence of SEQ ID NO. 22 (L-CDR2); and the amino acid sequence of SEQ ID NO. 24 (L-CDR3).

10. The anti-ANGPT2 antibody of claim 2, wherein the variable heavy chain comprises the amino acid sequence of SEQ ID NO. 3 and the variable light chain comprises the amino acid sequence of SEQ ID NO. 8.

11. The anti-ANGPT2 antibody of claim 2, wherein the variable heavy chain comprises the amino acid sequence of SEQ ID NO. 4 and the variable light chain comprises the amino acid sequence of SEQ ID NO. 9.

12. The anti-ANGPT2 antibody of claim 2, wherein the variable heavy chain comprises the amino acid sequence of SEQ ID NO. 5 and the variable light chain comprises the amino acid sequence of SEQ ID NO. 10.

13. The anti-ANGPT2 antibody of claim 2, wherein the variable heavy chain comprises the amino acid sequence of SEQ ID NO. 6 and the variable light chain comprises the amino acid sequence of SEQ ID NO. 11.

14. The anti-ANGPT2 antibody of claim 2, wherein the variable heavy chain comprises the amino acid sequence of SEQ ID NO. 7 and the variable light chain comprises the amino acid sequence of SEQ ID NO. 12.

15. An anti-ANGPT2 antibody comprising a heavy chain comprising SEQ ID NO. 31 and a light chain comprising SEQ ID NO. 32.

16. An anti-ANGPT2 antibody comprising a heavy chain comprising SEQ ID NO. 33 and a light chain comprising SEQ ID NO. 34.

17. An anti-ANGPT2 antibody comprising a heavy chain comprising SEQ ID NO. 35 and a light chain comprising SEQ ID NO. 36.

18. An anti-ANGPT2 antibody comprising a heavy chain comprising SEQ ID NO. 37 and a light chain comprising SEQ ID NO. 38.

19. An anti-ANGPT2 antibody comprising a heavy chain comprising SEQ ID NO. 39 and a light chain comprising SEQ ID NO. 40.

* * * * *

UNITED STATES PATENT AND TRADEMARK OFFICE
CERTIFICATE OF CORRECTION

| | | |
|---|---|---|
| PATENT NO. | : 11,396,539 B2 | |
| APPLICATION NO. | : 16/911419 | |
| DATED | : July 26, 2022 | |
| INVENTOR(S) | : Ryan Michael Fryer et al. | |

It is certified that error appears in the above-identified patent and that said Letters Patent is hereby corrected as shown below:

In the Drawings

Delete fig. 2 and substitute therefor the drawing sheet, consisting of fig. 2 as shown on the attached page.

Signed and Sealed this
Twenty-seventh Day of September, 2022

*Katherine Kelly Vidal*

Katherine Kelly Vidal
*Director of the United States Patent and Trademark Office*

SEQUENCE LISTING

<160> NUMBER OF SEQ ID NOS: 59

<210> SEQ ID NO 1
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Lys Gln Ser Gly Ala Glu Leu Val Lys Pro Gly Ser
1               5                   10                  15

Ser Val Lys Ile Ser Cys Arg Ala Ser Gly Tyr Ile Phe Ile Asp Tyr
            20                  25                  30

Phe Ile Asn Trp Val Lys Gln Arg Pro Gly Gln Gly Leu Glu Trp Ile
        35                  40                  45

Gly Lys Ile Gly Pro Gly Ser Gly Ser Ser Ser Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Glu Ala Phe Asp Tyr Asp Gly Asp Tyr Tyr Gly Met Ala Tyr
            100                 105                 110

Trp Gly Gln Gly Thr Ser Val Thr Val Ser Ser
        115                 120

<210> SEQ ID NO 2
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Phe Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Thr Ser Val Gln Ala Glu Asp Leu Ala Val Tyr Tyr Cys Gln Asn
                85                  90                  95

Asp His Ser Tyr Pro Ile Thr Phe Gly Ser Gly Thr Lys Leu Glu Ile
            100                 105                 110

Lys

<210> SEQ ID NO 3
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Ile Asp Tyr
            20                  25                  30

Phe Ile Asn Trp Val Arg Gln Ala Pro Gly Gln Gly Leu Glu Trp Met
        35                  40                  45

Gly Lys Ile Gly Pro Gly Ser Gly Ser Ser Ser Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Phe Asp Tyr Glu Gly Asp Tyr Tyr Gly Met Ala Tyr
            100                 105                 110

Trp Gly Gln Gly Thr Leu Val Thr Val Ser Ser
        115                 120

<210> SEQ ID NO 4
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Ile Glu Tyr
            20                  25                  30

Phe Ile Asn Trp Val Arg Gln Ala Pro Gly Gln Gly Leu Glu Trp Met
        35                  40                  45

Gly Lys Ile Gly Pro Gly Ser Gly Ser Ser Ser Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Phe Asp Tyr Glu Gly Asp Tyr Tyr Gly Met Ala Tyr
            100                 105                 110

Trp Gly Gln Gly Thr Leu Val Thr Val Ser Ser
        115                 120

<210> SEQ ID NO 5
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Ile Asp Tyr
            20                  25                  30

Phe Ile Asn Trp Val Arg Gln Ala Pro Gly Gln Gly Leu Glu Trp Met
            35                  40                  45

Gly Lys Ile Gly Pro Gly Ser Gly Ser Ser Ser Asn Glu Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Glu Ala Phe Asp Tyr Asp Gly Asp Tyr Tyr Gly Met Ala Tyr
            100                 105                 110

Trp Gly Gln Gly Thr Leu Val Thr Val Ser Ser
            115                 120

<210> SEQ ID NO 6
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ile Phe Ile Asp Tyr
                20                  25                  30

Phe Ile Asn Trp Val Arg Gln Ala Pro Gly Gln Gly Leu Glu Trp Met
            35                  40                  45

Gly Lys Ile Gly Pro Gly Ser Gly Ser Ser Ser Asn Glu Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Glu Ala Phe Asp Tyr Asp Gly Asp Tyr Tyr Gly Met Ala Tyr
            100                 105                 110

Trp Gly Gln Gly Thr Leu Val Thr Val Ser Ser
            115                 120

<210> SEQ ID NO 7
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ile Phe Ile Asp Tyr
                20                  25                  30

Phe Ile Asn Trp Val Arg Gln Ala Pro Gly Gln Gly Leu Glu Trp Met
            35                  40                  45

Gly Lys Ile Gly Pro Gly Ser Gly Ser Ser Ser Asn Glu Lys Phe
 50                  55                  60

Lys Gly Arg Val Thr Ile Thr Ala Asp Lys Ser Thr Ser Thr Ala Tyr
 65                  70                  75                  80

```
Met Glu Leu Ser Ser Leu Arg Ser Glu Asp Thr Ala Val Tyr Tyr Cys
                85                  90                  95

Ala Arg Glu Ala Phe Asp Tyr Asp Gly Asp Tyr Tyr Gly Met Ala Tyr
            100                 105                 110

Trp Gly Gln Gly Thr Leu Val Thr Val Ser Ser
        115                 120

<210> SEQ ID NO 8
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Ile Val Met Thr Gln Ser Pro Ala Thr Leu Ser Val Ser Pro Gly
1               5                   10                  15

Glu Arg Ala Thr Leu Ser Cys Lys Ser Gln Ser Leu Leu Ala Ser
            20                  25                  30

Gly Asn Gln Lys Asn Phe Leu Ala Trp Tyr Gln Gln Lys Pro Gly Gln
        35                  40                  45

Ala Pro Arg Leu Leu Ile Tyr Gly Ala Ser Thr Arg Glu Ser Gly Ile
    50                  55                  60

Pro Ala Arg Phe Ser Gly Ser Gly Ser Gly Thr Glu Phe Thr Leu Thr
65                  70                  75                  80

Ile Ser Ser Leu Gln Ser Glu Asp Phe Ala Val Tyr Tyr Cys Gln Asn
                85                  90                  95

Asp His Ser Tyr Pro Ile Thr Phe Gly Gln Gly Thr Lys Leu Glu Ile
            100                 105                 110

Lys

<210> SEQ ID NO 9
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Ile Val Met Thr Gln Ser Pro Ala Thr Leu Ser Val Ser Pro Gly
1               5                   10                  15

Glu Arg Ala Thr Leu Ser Cys Lys Ser Gln Ser Leu Leu Ala Ser
            20                  25                  30

Gly Asn Gln Lys Asn Phe Leu Ala Trp Tyr Gln Gln Lys Pro Gly Gln
        35                  40                  45

Ala Pro Arg Leu Leu Ile Tyr Gly Ala Ser Thr Arg Glu Ser Gly Ile
    50                  55                  60

Pro Ala Arg Phe Ser Gly Ser Gly Ser Gly Thr Glu Phe Thr Leu Thr
65                  70                  75                  80

Ile Ser Ser Leu Gln Ser Glu Asp Phe Ala Val Tyr Tyr Cys Gln Asn
                85                  90                  95

Asp His Ser Tyr Pro Ile Thr Phe Gly Gln Gly Thr Lys Leu Glu Ile
            100                 105                 110

Lys

<210> SEQ ID NO 10
```

<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Glu Ile Val Met Thr Gln Ser Pro Ala Thr Leu Ser Val Ser Pro Gly
1               5                   10                  15

Glu Arg Ala Thr Leu Ser Cys Lys Ser Ser Gln Ser Leu Leu Ser Ser
            20                  25                  30

Gly Asn Gln Lys Ser Phe Leu Ala Trp Tyr Gln Gln Lys Pro Gly Gln
        35                  40                  45

Ala Pro Arg Leu Leu Ile Tyr Gly Ala Ser Thr Arg Glu Thr Gly Ile
    50                  55                  60

Pro Ala Arg Phe Ser Gly Ser Gly Ser Gly Thr Glu Phe Thr Leu Thr
65                  70                  75                  80

Ile Ser Ser Leu Gln Ser Glu Asp Phe Ala Val Tyr Tyr Cys Gln Asn
                85                  90                  95

Asp His Ser Tyr Pro Ile Thr Phe Gly Gln Gly Thr Lys Leu Glu Ile
            100                 105                 110

Lys

<210> SEQ ID NO 11
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Leu Ser Ser
            20                  25                  30

Gly Asn Gln Lys Ser Phe Leu Ala Trp Tyr Gln Gln Lys Pro Gly Gln
        35                  40                  45

Ala Pro Arg Leu Leu Ile Tyr Gly Ala Ser Thr Arg Glu Thr Gly Ile
    50                  55                  60

Pro Ala Arg Phe Ser Gly Ser Gly Ser Gly Thr Glu Phe Thr Leu Thr
65                  70                  75                  80

Ile Ser Ser Leu Gln Ser Glu Asp Phe Ala Val Tyr Tyr Cys Gln Gln
                85                  90                  95

Asp His Ser Tyr Pro Ile Thr Phe Gly Gln Gly Thr Lys Leu Glu Ile
            100                 105                 110

Lys

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Glu Ile Val Met Thr Gln Ser Pro Ala Thr Leu Ser Val Ser Pro Gly
1               5                   10                  15

```
Glu Arg Ala Thr Leu Ser Cys Lys Ser Ser Gln Ser Leu Leu Ser Ser
                20                  25                  30
Gly Asn Gln Lys Ser Phe Leu Ala Trp Tyr Gln Gln Lys Pro Gly Gln
            35                  40                  45
Ala Pro Arg Leu Leu Ile Tyr Gly Ala Ser Thr Arg Glu Ser Gly Ile
 50                  55                  60
Pro Ala Arg Phe Ser Gly Ser Gly Ser Gly Thr Glu Phe Thr Leu Thr
 65                  70                  75                  80
Ile Ser Ser Leu Gln Ser Glu Asp Phe Ala Val Tyr Cys Gln Asn
                85                  90                  95
Asp His Ser Tyr Pro Ile Thr Phe Gly Gln Gly Thr Lys Leu Glu Ile
                100                 105                 110
Lys

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Tyr Ile Phe Ile Asp Tyr Phe Ile Asn
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Tyr Ile Phe Ile Glu Tyr Phe Ile Asn
 1               5                  10

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Ile Gly Pro Gly Ser Gly Ser Ser Ser Asn Glu Lys Phe Lys
 1               5                  10                  15
Gly

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Ala Phe Asp Tyr Asp Gly Asp Tyr Tyr Gly Met Ala Tyr
 1               5                  10
```

```
<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Ala Phe Asp Tyr Glu Gly Asp Tyr Tyr Gly Met Ala Tyr
1               5                  10

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Ser Ser Gln Ser Leu Leu Asn Ser Gly Asn Gln Lys Asn Phe Leu
1               5                  10                  15

Ala

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Ser Ser Gln Ser Leu Leu Ala Ser Gly Asn Gln Lys Asn Phe Leu
1               5                  10                  15

Ala

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Ser Ser Gln Ser Leu Leu Ser Ser Gly Asn Gln Lys Ser Phe Leu
1               5                  10                  15

Ala

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ala Ser Gln Ser Val Leu Ser Ser Gly Asn Gln Lys Ser Phe Leu
1               5                  10                  15

Ala
```

```
<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ala Ser Thr Arg Glu Ser
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Ala Ser Thr Arg Glu Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Asn Asp His Ser Tyr Pro Ile Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Gln Asp His Ser Tyr Pro Ile Thr
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Tyr Phe Ile Asn
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

```
Glu Tyr Phe Ile Asn
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Tyr Ile Phe Ile Asp Tyr
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Tyr Ile Phe Ile Glu Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Pro Gly Ser Gly Ser
1               5

<210> SEQ ID NO 31
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Ile Asp Tyr
                20                  25                  30

Phe Ile Asn Trp Val Arg Gln Ala Pro Gly Gln Gly Leu Glu Trp Met
            35                  40                  45

Gly Lys Ile Gly Pro Gly Ser Gly Ser Ser Ser Asn Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Phe Asp Tyr Glu Gly Asp Tyr Tyr Gly Met Ala Tyr
            100                 105                 110

Trp Gly Gln Gly Thr Leu Val Thr Val Ser Ser Ala Ser Thr Lys Gly
```

115                 120                 125
Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 32
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Ile Val Met Thr Gln Ser Pro Ala Thr Leu Ser Val Ser Pro Gly
1               5                   10                  15

```
Glu Arg Ala Thr Leu Ser Cys Lys Ser Ser Gln Ser Leu Leu Ala Ser
                20                  25                  30

Gly Asn Gln Lys Asn Phe Leu Ala Trp Tyr Gln Lys Pro Gly Gln
            35                  40                  45

Ala Pro Arg Leu Leu Ile Tyr Gly Ala Ser Thr Arg Glu Ser Gly Ile
 50                  55                  60

Pro Ala Arg Phe Ser Gly Ser Gly Ser Gly Thr Glu Phe Thr Leu Thr
 65                  70                  75                  80

Ile Ser Ser Leu Gln Ser Glu Asp Phe Ala Val Tyr Tyr Cys Gln Asn
                85                  90                  95

Asp His Ser Tyr Pro Ile Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 33
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Ile Glu Tyr
                20                  25                  30

Phe Ile Asn Trp Val Arg Gln Ala Pro Gly Gln Gly Leu Glu Trp Met
            35                  40                  45

Gly Lys Ile Gly Pro Gly Ser Gly Ser Ser Ser Asn Glu Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Glu Ala Phe Asp Tyr Glu Gly Asp Tyr Tyr Gly Met Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly
    450

<210> SEQ ID NO 34
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Ile Val Met Thr Gln Ser Pro Ala Thr Leu Ser Val Ser Pro Gly
1               5                   10                  15

Glu Arg Ala Thr Leu Ser Cys Lys Ser Ser Gln Ser Leu Leu Ala Ser
            20                  25                  30

Gly Asn Gln Lys Asn Phe Leu Ala Trp Tyr Gln Gln Lys Pro Gly Gln
        35                  40                  45

Ala Pro Arg Leu Leu Ile Tyr Gly Ala Ser Thr Arg Glu Ser Gly Ile
```

```
                 50                  55                  60
Pro Ala Arg Phe Ser Gly Ser Gly Ser Gly Thr Glu Phe Thr Leu Thr
 65                  70                  75                  80

Ile Ser Ser Leu Gln Ser Glu Asp Phe Ala Val Tyr Tyr Cys Gln Asn
                     85                  90                  95

Asp His Ser Tyr Pro Ile Thr Phe Gly Gln Gly Thr Lys Leu Glu Ile
                    100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                    165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 35
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ile Phe Ile Asp Tyr
                 20                  25                  30

Phe Ile Asn Trp Val Arg Gln Ala Pro Gly Gln Gly Leu Glu Trp Met
             35                  40                  45

Gly Lys Ile Gly Pro Gly Ser Gly Ser Ser Ser Asn Glu Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ala Phe Asp Tyr Asp Gly Asp Tyr Tyr Gly Met Ala Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                    165                 170                 175

Pro Ala Val Leu Gln Ser Ser Gly Leu Tyr Ser Leu Ser Ser Val Val
                180                 185                 190
```

```
Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 36
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Ile Val Met Thr Gln Ser Pro Ala Thr Leu Ser Val Ser Pro Gly
1               5                   10                  15

Glu Arg Ala Thr Leu Ser Cys Lys Ser Ser Gln Ser Leu Leu Ser Ser
            20                  25                  30

Gly Asn Gln Lys Ser Phe Leu Ala Trp Tyr Gln Gln Lys Pro Gly Gln
        35                  40                  45

Ala Pro Arg Leu Leu Ile Tyr Gly Ala Ser Thr Arg Glu Thr Gly Ile
    50                  55                  60

Pro Ala Arg Phe Ser Gly Ser Gly Ser Gly Thr Glu Phe Thr Leu Thr
65                  70                  75                  80

Ile Ser Ser Leu Gln Ser Glu Asp Phe Ala Val Tyr Tyr Cys Gln Asn
                85                  90                  95
```

Asp His Ser Tyr Pro Ile Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 37
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Ile Asp Tyr
            20                  25                  30

Phe Ile Asn Trp Val Arg Gln Ala Pro Gly Gln Gly Leu Glu Trp Met
        35                  40                  45

Gly Lys Ile Gly Pro Gly Ser Gly Ser Ser Ser Asn Glu Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Phe Asp Tyr Asp Gly Asp Tyr Tyr Gly Met Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu

```
                225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly
            450

<210> SEQ ID NO 38
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Leu Ser Ser
            20                  25                  30

Gly Asn Gln Lys Ser Phe Leu Ala Trp Tyr Gln Gln Lys Pro Gly Gln
        35                  40                  45

Ala Pro Arg Leu Leu Ile Tyr Gly Ala Ser Thr Arg Glu Thr Gly Ile
    50                  55                  60

Pro Ala Arg Phe Ser Gly Ser Gly Ser Gly Thr Glu Phe Thr Leu Thr
65                  70                  75                  80

Ile Ser Ser Leu Gln Ser Glu Asp Phe Ala Val Tyr Tyr Cys Gln Gln
                85                  90                  95

Asp His Ser Tyr Pro Ile Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125
```

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 39
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Ile Asp Tyr
            20                  25                  30

Phe Ile Asn Trp Val Arg Gln Ala Pro Gly Gln Gly Leu Glu Trp Met
            35                  40                  45

Gly Lys Ile Gly Pro Gly Ser Gly Ser Ser Ser Asn Glu Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Glu Ala Phe Asp Tyr Asp Gly Asp Tyr Tyr Gly Met Ala Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
         275                 280                 285

Glu Val His Asn Ala Lys Thr Lys Pro Arg Glu Glu Gln Tyr Asn Ser
         290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                 325                 330                 335

Pro Ile Glu Lys Thr Ile Ser Lys Ala Lys Gly Gln Pro Arg Glu Pro
             340                 345                 350

Gln Val Tyr Thr Leu Pro Pro Ser Arg Glu Glu Met Thr Lys Asn Gln
         355                 360                 365

Val Ser Leu Thr Cys Leu Val Lys Gly Phe Tyr Pro Ser Asp Ile Ala
     370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                 405                 410                 415

Thr Val Asp Lys Ser Arg Trp Gln Gln Gly Asn Val Phe Ser Cys Ser
             420                 425                 430

Val Met His Glu Ala Leu His Asn His Tyr Thr Gln Lys Ser Leu Ser
         435                 440                 445

Leu Ser Pro Gly
        450

<210> SEQ ID NO 40
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Ile Val Met Thr Gln Ser Pro Ala Thr Leu Ser Val Ser Pro Gly
1               5                   10                  15

Glu Arg Ala Thr Leu Ser Cys Lys Ser Ser Gln Ser Leu Leu Ser Ser
             20                  25                  30

Gly Asn Gln Lys Ser Phe Leu Ala Trp Tyr Gln Gln Lys Pro Gly Gln
         35                  40                  45

Ala Pro Arg Leu Leu Ile Tyr Gly Ala Ser Thr Arg Glu Ser Gly Ile
50                  55                  60

Pro Ala Arg Phe Ser Gly Ser Gly Ser Gly Thr Glu Phe Thr Leu Thr
65                  70                  75                  80

Ile Ser Ser Leu Gln Ser Glu Asp Phe Ala Val Tyr Tyr Cys Gln Asn
                 85                  90                  95

Asp His Ser Tyr Pro Ile Thr Phe Gly Gln Gly Thr Lys Leu Glu Ile
             100                 105                 110

Lys Arg Thr Val Ala Ala Pro Ser Val Phe Ile Phe Pro Pro Ser Asp
         115                 120                 125

Glu Gln Leu Lys Ser Gly Thr Ala Ser Val Val Cys Leu Leu Asn Asn
     130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp

```
                    165                 170                 175
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 41
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Trp Val Arg Gln Ala Pro Gly Gln Gly Leu Glu Trp Met Gly
1               5                   10

<210> SEQ ID NO 43
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Trp Gly Gln Gly Thr Leu Val Thr Val Ser Ser
1               5                   10

<210> SEQ ID NO 45
<211> LENGTH: 23
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 45

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Trp Tyr Gln Gln Lys Pro Gly Gln Ala Pro Arg Leu Leu Ile Tyr
1               5                   10                  15

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Gly Gln Gly Thr Lys Leu Glu Ile Lys
1               5                   10

<210> SEQ ID NO 49
<211> LENGTH: 495
<212> TYPE: PRT
<213> ORGANISM: Homo sapiens

<400> SEQUENCE: 49

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

```
Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
                100                 105                 110

Gln Gln Asn Ala Val Gln Asn Gln Thr Ala Val Met Ile Glu Ile Gly
                115                 120                 125

Thr Asn Leu Leu Asn Gln Thr Ala Glu Gln Thr Arg Lys Leu Thr Asp
            130                 135                 140

Val Glu Ala Gln Val Leu Asn Gln Thr Thr Arg Glu Leu Gln Leu Leu
145                 150                 155                 160

Glu His Ser Leu Ser Thr Asn Lys Leu Glu Lys Gln Ile Leu Asp Gln
                165                 170                 175

Thr Ser Glu Ile Asn Lys Leu Gln Asp Lys Asn Ser Phe Leu Glu Lys
                180                 185                 190

Lys Val Leu Ala Met Glu Asp Lys His Ile Ile Gln Leu Gln Ser Ile
            195                 200                 205

Lys Glu Glu Lys Asp Gln Leu Gln Val Leu Val Ser Lys Gln Asn Ser
            210                 215                 220

Ile Ile Glu Glu Leu Glu Lys Lys Ile Val Thr Ala Thr Val Asn Asn
225                 230                 235                 240

Ser Val Leu Gln Lys Gln Gln His Asp Leu Met Glu Thr Val Asn Asn
                245                 250                 255

Leu Leu Thr Met Met Ser Thr Ser Asn Ser Ala Lys Asp Pro Thr Val
                260                 265                 270

Ala Lys Glu Glu Gln Ile Ser Phe Arg Asp Cys Ala Glu Val Phe Lys
            275                 280                 285

Ser Gly His Thr Thr Asn Gly Ile Tyr Thr Leu Thr Phe Pro Asn Ser
            290                 295                 300

Thr Glu Glu Ile Lys Ala Tyr Cys Asp Met Glu Ala Gly Gly Gly Gly
305                 310                 315                 320

Trp Thr Ile Ile Gln Arg Arg Glu Asp Gly Ser Val Asp Phe Gln Arg
                325                 330                 335

Thr Trp Lys Glu Tyr Lys Val Gly Phe Gly Asn Pro Ser Gly Glu Tyr
                340                 345                 350

Trp Leu Gly Asn Glu Phe Val Ser Gln Leu Thr Asn Gln Gln Arg Tyr
            355                 360                 365

Val Leu Lys Ile His Leu Lys Asp Trp Glu Gly Asn Glu Ala Tyr Ser
            370                 375                 380

Leu Tyr Glu His Phe Tyr Leu Ser Ser Glu Glu Leu Asn Tyr Arg Ile
385                 390                 395                 400

His Leu Lys Gly Leu Thr Gly Thr Ala Gly Lys Ile Ser Ser Ile Ser
                405                 410                 415

Gln Pro Gly Asn Asp Phe Ser Thr Lys Asp Gly Asp Asn Asp Lys Cys
                420                 425                 430

Ile Cys Lys Cys Ser Gln Met Leu Thr Gly Gly Trp Trp Phe Asp Ala
            435                 440                 445

Cys Gly Pro Ser Asn Leu Asn Gly Met Tyr Tyr Pro Gln Arg Gln Asn
            450                 455                 460

Thr Asn Lys Phe Asn Gly Ile Lys Trp Tyr Tyr Trp Lys Gly Ser Gly
465                 470                 475                 480

Tyr Ser Leu Lys Ala Thr Thr Met Met Ile Arg Pro Ala Asp Phe
                485                 490                 495
```

```
<210> SEQ ID NO 50
<211> LENGTH: 222
<212> TYPE: PRT
<213> ORGANISM: Homo sapiens

<400> SEQUENCE: 50

Lys Glu Glu Gln Ile Ser Phe Arg Asp Cys Ala Glu Val Phe Lys Ser
1               5                   10                  15

Gly His Thr Thr Asn Gly Ile Tyr Thr Leu Thr Phe Pro Asn Ser Thr
            20                  25                  30

Glu Glu Ile Lys Ala Tyr Cys Asp Met Glu Ala Gly Gly Gly Gly Trp
        35                  40                  45

Thr Ile Ile Gln Arg Arg Glu Asp Gly Ser Val Asp Phe Gln Arg Thr
    50                  55                  60

Trp Lys Glu Tyr Lys Val Gly Phe Gly Asn Pro Ser Gly Glu Tyr Trp
65                  70                  75                  80

Leu Gly Asn Glu Phe Val Ser Gln Leu Thr Asn Gln Gln Arg Tyr Val
                85                  90                  95

Leu Lys Ile His Leu Lys Asp Trp Glu Gly Asn Glu Ala Tyr Ser Leu
            100                 105                 110

Tyr Glu His Phe Tyr Leu Ser Ser Glu Glu Leu Asn Tyr Arg Ile His
        115                 120                 125

Leu Lys Gly Leu Thr Gly Thr Ala Gly Lys Ile Ser Ser Ile Ser Gln
    130                 135                 140

Pro Gly Asn Asp Phe Ser Thr Lys Asp Gly Asp Asn Asp Lys Cys Ile
145                 150                 155                 160

Cys Lys Cys Ser Gln Met Leu Thr Gly Gly Trp Trp Phe Asp Ala Cys
                165                 170                 175

Gly Pro Ser Asn Leu Asn Gly Met Tyr Tyr Pro Gln Arg Gln Asn Thr
            180                 185                 190

Asn Lys Phe Asn Gly Ile Lys Trp Tyr Tyr Trp Lys Gly Ser Gly Tyr
        195                 200                 205

Ser Leu Lys Ala Thr Thr Met Met Ile Arg Pro Ala Asp Phe
    210                 215                 220

<210> SEQ ID NO 51
<211> LENGTH: 32
<212> TYPE: PRT
<213> ORGANISM: Homo sapiens

<400> SEQUENCE: 51

Tyr Leu Ser Ser Glu Glu Leu Asn Tyr Arg Ile His Leu Lys Gly Leu
1               5                   10                  15

Thr Gly Thr Ala Gly Lys Ile Ser Ser Ile Ser Gln Pro Gly Asn Asp
            20                  25                  30

<210> SEQ ID NO 52
<211> LENGTH: 67
<212> TYPE: PRT
<213> ORGANISM: Homo sapiens

<400> SEQUENCE: 52

Phe Ser Thr Lys Asp Gly Asp Asn Asp Lys Cys Ile Cys Lys Cys Ser
1               5                   10                  15

Gln Met Leu Thr Gly Gly Trp Trp Phe Asp Ala Cys Gly Pro Ser Asn
            20                  25                  30

Leu Asn Gly Met Tyr Tyr Pro Gln Arg Gln Asn Thr Asn Lys Phe Asn
        35                  40                  45
```

-continued

```
Gly Ile Lys Trp Tyr Tyr Trp Lys Gly Ser Gly Tyr Ser Leu Lys Ala
        50                  55                  60

Thr Thr Met
65

<210> SEQ ID NO 53
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Thr Gly Lys Gly Leu Glu Trp Val
        35                  40                  45

Ser Ala Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Leu Ile Thr Phe Gly Gly Leu Ile Ala Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
```

```
                    325                 330                 335
Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys Glu Val Gln Leu Val
            450                 455

<210> SEQ ID NO 54
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asp Asn Ser Gln
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 55
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Gly Met His Trp Val Arg Gln Ala Pro Gly Lys Gly Leu Glu Trp Val
        35                  40                  45

Ala Val Ile Ser His Asp Gly Asn Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Asp Phe Trp Ser Gly Leu Asn Trp Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

```
Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 56
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Thr Gly Ala Ser Ser Trp Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 57
<211> LENGTH: 459
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 57

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
            115                 120                 125

Ser Ala Ser Thr Lys Gly Pro Ser Val Phe Pro Leu Ala Pro Ser Ser
130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400
```

```
Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 58
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 59
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Lys Glu Glu Gln Ile Ser Phe Arg Asp Cys Ala Glu Val Phe Lys Ser
1               5                   10                  15
```

-continued

```
Gly His Thr Thr Asn Gly Ile Tyr Thr Leu Thr Phe Pro Asn Ser Thr
             20                  25                  30

Glu Glu Ile Lys Ala Tyr Cys Asp Met Glu Ala Gly Gly Gly Gly Trp
         35              40                  45

Thr Ile Ile Gln Arg Arg Glu Asp Gly Ser Val Asp Phe Gln Arg Thr
         50                  55                  60

Trp Lys Glu Tyr Lys Val Gly Phe Gly Asn Pro Ser Gly Glu Tyr Trp
65                   70                  75                  80

Leu Gly Asn Glu Phe Val Ser Gln Leu Thr Asn Gln Gln Arg Tyr Val
                 85                  90                  95

Leu Lys Ile His Leu Lys Asp Trp Glu Gly Asn Glu Ala Tyr Ser Leu
             100                 105                 110

Tyr Glu His Phe Tyr Leu Ser Ser Glu Glu Leu Asn Tyr Arg Ile His
         115                 120                 125

Leu Lys Gly Leu Thr Gly Thr Ala Gly Lys Ile Ser Ser Ile Ser Gln
    130                 135                 140

Pro Gly Asn Asp Phe Ser Thr Lys Asp Gly Asp Asn Asp Lys Cys Ile
145                 150                 155                 160

Cys Lys Cys Ser Gln Met Leu Thr Gly Gly Trp Trp Phe Asp Ala Cys
                165                 170                 175

Gly Pro Ser Asn Leu Asn Gly Met Tyr Tyr Pro Gln Arg Gln Asn Thr
            180                 185                 190

Asn Lys Phe Asn Gly Ile Lys Trp Tyr Tyr Trp Lys Gly Ser Gly Tyr
        195                 200                 205

Ser Leu Lys Ala Thr Thr Met Met Ile Arg Pro Ala Asp Phe
    210                 215                 220
```